US011980716B2

(12) United States Patent
Lee et al.

(10) Patent No.: US 11,980,716 B2
(45) Date of Patent: May 14, 2024

(54) PATIENT INTERFACE COMPRISING A GAS WASHOUT VENT

(71) Applicant: ResMed Pty Ltd, Bella Vista (AU)

(72) Inventors: Cheoung Hong Lee, Singapore (SG); Robin Yew, Singapore (SG)

(73) Assignee: ResMed Pty Ltd, Bella Vista (AU)

( * ) Notice: Subject to any disclaimer, the term of this patent is extended or adjusted under 35 U.S.C. 154(b) by 959 days.

(21) Appl. No.: 16/941,714

(22) Filed: Jul. 29, 2020

(65) Prior Publication Data
US 2020/0353189 A1 Nov. 12, 2020

Related U.S. Application Data

(63) Continuation of application No. 15/546,793, filed as application No. PCT/AU2016/050045 on Jan. 29, 2016, now Pat. No. 10,765,824.
(Continued)

(30) Foreign Application Priority Data
Jan. 30, 2015 (AU) ................ 2015900281

(51) Int. Cl.
*A61M 16/06* (2006.01)
*A61M 16/00* (2006.01)
(Continued)

(52) U.S. Cl.
CPC .......... *A61M 16/06* (2013.01); *A61M 16/009* (2013.01); *A61M 16/0616* (2014.02);
(Continued)

(58) Field of Classification Search
CPC .............. A61M 16/0066; A61M 16/06; A61M 16/0605; A61M 16/0616; A61M 16/0622;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

WO WO 98/04310 A1 2/1998
WO WO 98/34665 A1 8/1998
(Continued)

OTHER PUBLICATIONS

International Search Report for PCT/AU2016/050045 dated May 4, 2016, 4 pages.
(Continued)

*Primary Examiner* — Joseph D. Boecker
(74) *Attorney, Agent, or Firm* — Nixon & Vanderhye P.C.

(57) ABSTRACT

A gas washout vent for a patient interface may be configured to allow a flow of patient exhaled gas to an exterior of the patient interface to minimise rebreathing of exhaled gas by the patient and the vent may include: a plurality of vent passages extending between a first and a second side of the vent, each vent passage may include: a plurality of first openings extending from the first side towards the second side, said first openings being uniform in size and shape; a plurality of second openings extending from the second side towards the first side, said second openings being uniform in size and shape; and wherein the first openings and the second openings partially overlap each other at an interface to form constricted passages therebetween.

18 Claims, 29 Drawing Sheets

Related U.S. Application Data

(60) Provisional application No. 62/263,278, filed on Dec. 4, 2015.

(51) Int. Cl.
 *A61M 16/10* (2006.01)
 *A61M 16/16* (2006.01)

(52) U.S. Cl.
 CPC ........ *A61M 16/1065* (2014.02); *A61M 16/16* (2013.01); *A61M 16/107* (2014.02); *A61M 2202/0225* (2013.01); *A61M 2205/3344* (2013.01); *A61M 2205/42* (2013.01); *A61M 2207/00* (2013.01)

(58) Field of Classification Search
 CPC .......... A61M 16/0666; A61M 16/0816; A61M 16/0875; A61M 2202/0225; A61M 2202/52
 See application file for complete search history.

(56) References Cited

U.S. PATENT DOCUMENTS

| | | | |
|---|---|---|---|
| 6,460,539 B1 | 10/2002 | Japuntich et al. | |
| 6,532,959 B1 | 3/2003 | Berthon-Jones | |
| 6,561,190 B1 | 5/2003 | Kwok | |
| 6,581,594 B1 | 6/2003 | Drew et al. | |
| 6,662,803 B2 | 12/2003 | Gradon et al. | |
| 6,848,443 B2 | 2/2005 | Schmidt et al. | |
| 7,866,944 B2 | 1/2011 | Kenyon et al. | |
| 8,397,727 B2 | 3/2013 | Ng et al. | |
| 8,528,558 B2 | 9/2013 | Drew et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,820,325 B2 | 9/2014 | Breen | |
| 10,765,824 B2 * | 9/2020 | Lee .................. | A61M 16/1065 |
| 2002/0092527 A1 | 7/2002 | Wood | |
| 2003/0005931 A1 | 1/2003 | Jaffre | |
| 2004/0094157 A1 | 5/2004 | Dantanarayana | |
| 2008/0276937 A1 | 11/2008 | Davidson | |
| 2009/0044808 A1 | 2/2009 | Guney et al. | |
| 2009/0044810 A1 * | 2/2009 | Kwok ............... | A61M 16/0633 128/206.28 |
| 2009/0050156 A1 * | 2/2009 | Ng .................... | A61M 16/0816 128/205.24 |
| 2010/0000534 A1 | 1/2010 | Kooij et al. | |
| 2010/0051034 A1 | 3/2010 | Howard | |
| 2010/0154798 A1 | 6/2010 | Henry et al. | |
| 2011/0011397 A1 * | 1/2011 | Ziv .................... | A61M 16/06 128/207.18 |
| 2011/0082380 A1 * | 4/2011 | Breen ............... | A61M 16/0866 128/203.12 |
| 2011/0240030 A1 | 10/2011 | Ho | |
| 2013/0199538 A1 * | 8/2013 | Lockhart ........... | A61M 16/06 128/205.25 |
| 2014/0174446 A1 | 6/2014 | Prentice | |
| 2015/0217074 A1 | 8/2015 | Wells et al. | |
| 2016/0008558 A1 | 1/2016 | Huddart | |
| 2016/0008566 A1 * | 1/2016 | Partington ........ | A61M 16/1045 128/205.12 |
| 2016/0074605 A1 * | 3/2016 | Lin ................... | A61M 16/0069 128/204.23 |
| 2016/0310688 A1 | 10/2016 | Rothermel | |
| 2018/0015243 A1 | 1/2018 | Lee et al. | |
| 2019/0160249 A1 | 5/2019 | Rose | |

FOREIGN PATENT DOCUMENTS

| | | |
|---|---|---|
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2011/142678 A1 | 11/2011 |
| WO | WO 2012/171072 A1 | 12/2012 |
| WO | WO 2013/020167 A1 | 2/2013 |
| WO | WO-2014015382 A1 * | 1/2014 ............ A61M 16/06 |

OTHER PUBLICATIONS

Written Opinion of the ISA for PCT/AU2016/050045 dated May 4, 2016, 10 pages.
International Preliminary Report on Patentability for PCT/AU2016/050045 dated May 18, 2017, 40 pages.
West, John B., "Respiratory Physiology", Lippincott Williams & Wilkins, 9th edition published 2012, 8 pages.

* cited by examiner

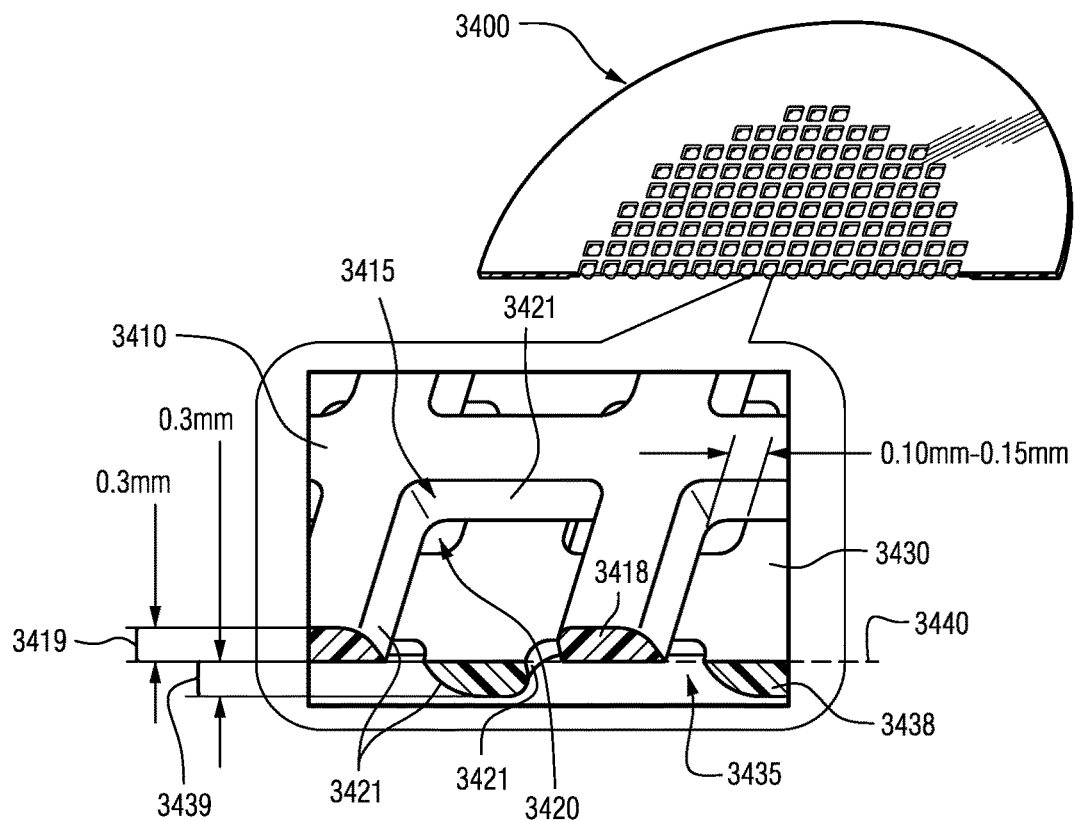
Fig. 7H
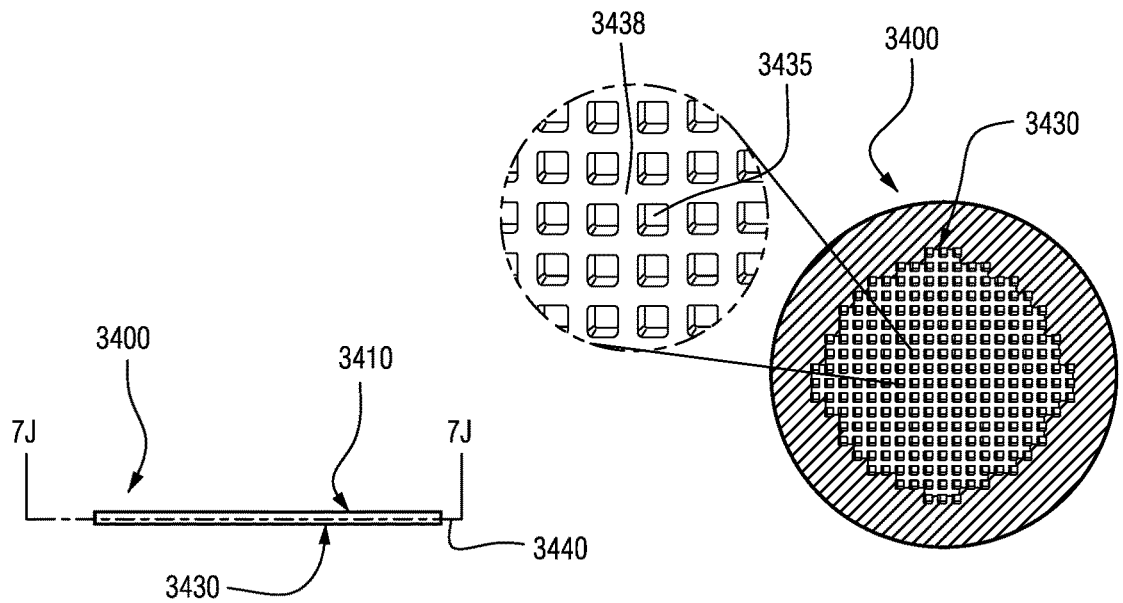
Fig. 7I
Fig. 7J

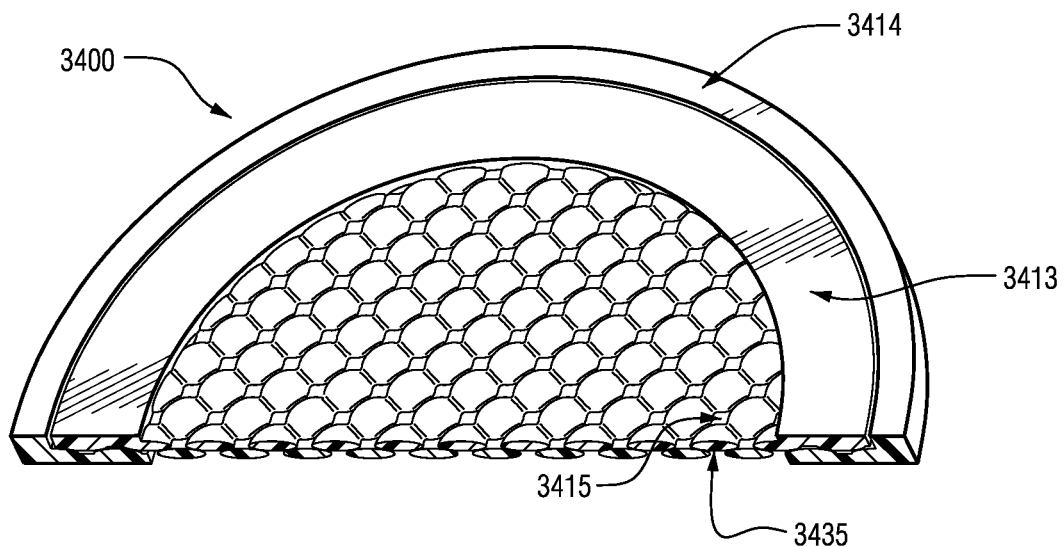
Fig. 8B
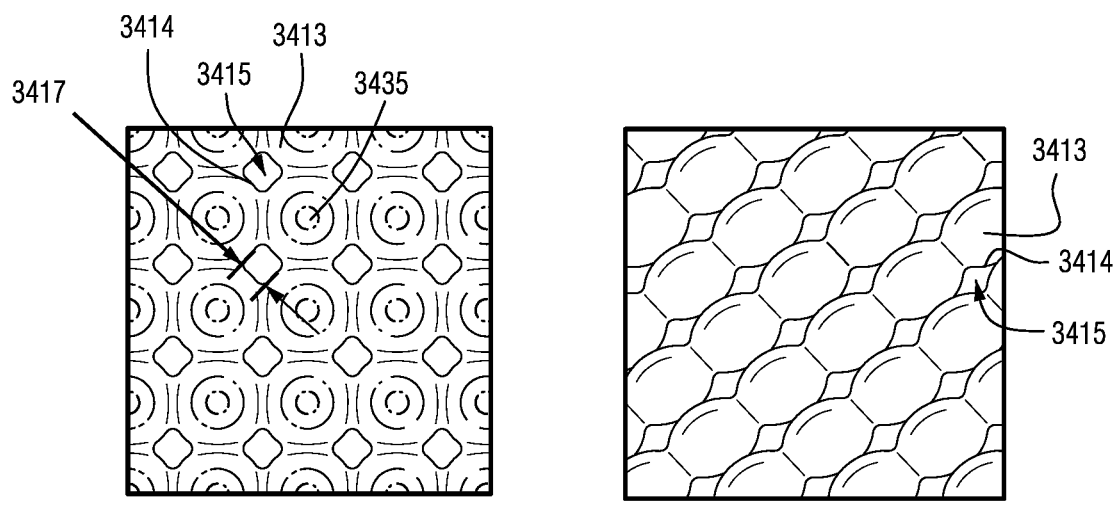
Fig. 8C
Fig. 8D

PATIENT INTERFACE COMPRISING A GAS WASHOUT VENT

1 CROSS-REFERENCE TO RELATED APPLICATIONS

This application is a continuation of U.S. application Ser. No. 15/546,793, filed Jul. 27, 2017, now U.S. Pat. No. 10,765,824, which is the U.S. national phase of International Application No. PCT/AU2016/050045, filed Jan. 29, 2016, which designated the U.S. and claims the benefit of U.S. Provisional Application No. 62/263,278, filed Dec. 4, 2015, and Australian Provisional Application No. 2015900281, filed on Jan. 30, 2015, the entire contents of each of which are incorporated herein by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and Its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR), Obesity Hyperventilation Syndrome (OHS), Chronic Obstructive Pulmonary Disease (COPD), Neuromuscular Disease (NMD), and Chest wall disorders are examples of respiratory disorders or disorders that have relationships thereto.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH₂O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Sound pressure values of a variety of objects are listed below | | | | |
|---|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO3744 in CPAP mode at 10 cmH$_2$O)

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

A plurality of smaller vent holes may result in quieter and more diffuse vent flow in comparison to large vent holes. Generally, small vent holes are formed by moulding them around a plurality of thin pins as part of a moulding tool. However, thin pins usually result in breakage following prolonged use and therefore affect the reliability and robustness of the tool. Thus there is a need to produce smaller vent holes more reliably. Moreover, small vent holes may lead to blockage by water droplets formed in the vent holes under for example humidified respiratory pressure therapy. Thus, there is also a need to reduce the risk of this form of blockage.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cmH$_2$O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a gas washout vent for a patient interface, the vent configured to allow a flow of patient exhaled gas to an exterior of the patient interface to minimise rebreathing of exhaled gas by the patient, said vent comprising a plurality of vent passages extending between a first and second side of the vent. Each vent passage comprises a first opening extending from the first side towards the second side, and a second opening extending from the second side towards the first side, wherein the first and second openings only partially overlap each other along a plane to form a constricted passages therebetween. The plane may run through the constricted passages at the point where the first openings partially overlaps with the second openings and wherein the openings connect at the constricted passage to form the vent passage extending between the first and second sides. The vent may have a vertical axis running through the first and second sides and the plane may be perpendicular to the vertical axis running in between the first and second sides. Alternatively, the plane may be curved. The plane may be curved to correspond to the curvature of the patient interface. For example, the vent may be formed in the shell of the patient interface and the plane may be curved to correspond to the curvature of the shell. The plane may run through all the constricted passages. The first and second openings may extend towards each other but terminate at the plane. Small vent holes in traditional vents may become blocked by water droplets forming on the walls of the vent holes and blocking vent flow. In this form of the present technology, the constricted passage may be formed between at least one wall of the first opening and at least one wall of the second opening, wherein the at least one wall of the first opening extends from a first side of the plan towards the first side of the vent and the at least one wall of the second opening extends from a second side of the plane towards the second side of the vent. Thus, the constricted passage may be formed between at least two walls on different sides of a plane. This configuration may reduce the ability for water droplets to form between the walls of the constricted passage thereby reducing the risk of blockage under humidification. The partial overlap between the first and second openings also allows for the constricted passage to be formed from larger openings. The constricted passage forms a smaller passageway for the flow of exhaled air between the first and second openings, thereby constricted vent flow for noise muffling and increased diffuseness. The exhaled gases from the patient may flow through the larger first openings, through the constricted passage and into the second openings before exiting the gas washout vent and into the atmosphere. Additionally, each first opening may overlap a plurality of second openings to form a plurality of constricted passages. For example, each first opening may partially overlap four second openings to form four separate constricted passages. Thus, the flow of exhaled gas may flow into a single first opening then divide through a plurality of constricted passages, for example through four constricted passages, before flowing into a plurality of partially overlapping second openings to exit the gas washout vent. In this instance the vent flow of exhaled air may divide into a plurality of constricted flow paths for noise muffling and added diffuseness.

Another aspect of one form of the present technology is the gas washout vent for a patient interface, the vent configured to allow a flow of patient exhaled gas to an exterior of the patient interface to minimise rebreathing of exhaled gas by the patient, said vent comprising a plurality of vent passages formed by a wall extending between a first and second side of the vent. Each vent passage comprises a first opening formed by the wall extending from the first side towards the second side, and a second opening formed by the wall extending from the second side towards the first side, wherein the wall transitions between the first opening to the second opening by a stepped cross section to form a constricted passage therebetween.

Another aspect of one form of the present technology is the gas washout vent, wherein the first and/or second openings have a substantially constant cross sectional area that is larger than a cross sectional area of the constricted passage. The cross sectional area of the first and/or second openings may be modified to alter the vent flow noise characteristics and diffuseness of the flow of exhaled gas through the first openings. A constant cross sectional area may provide desired substantially constant flow characteristics through the first and/or second openings. Having a substantially constant cross sectional area of the first opening may also assist in ease of manufacturability when moulding the openings using a moulding tool with pins having a substantially constant cross sectional area. For example, the first openings may be substantially cylindrical, cube or cuboid in shape. Alternatively, the substantially constant cross sectional area may be formed by at least one curved wall. The at least one wall of the first and second openings may direct the flow of exhaled gases in manner to reduce noise and increase diffuseness. The constant cross sectional area of each first or second opening may be between 0.3 to 1 mm2. This cross sectional area allows for the openings to be moulded using a moulding tool having pins of a sufficient thickness to ensure durability and reliability upon prolonged repeated use. Preferably, the constant cross sectional area of the first or second opening may be 0.5 mm2. The cross sectional area of the constricted passage may be between 0.05 to 0.2 mm2. Preferably the cross sectional area of the constricted passage may be 0.1 mm2. In traditional smaller hole vents, blockage may occur under humidification as water droplets on the walls forming the vent holes and block the vent flow. The constricted passage formed by the partially overlapping first and second openings reduces the risk of blockage as the constricted passage is formed between first and second openings having a larger cross sectional area than the constricted passage. For example, having a cross sectional area of 0.3 to 1 $mm^2$ may be sufficiently large enough to prevent blockage under humidification as the space provided between the walls of the opening may prevent water droplets from blocking the opening. Thus, the constricted passage in this form of the present technology allows for obtaining the benefits of a smaller hole vent whilst reducing the risk of blockage under humidification.

Another aspect of one form of the present technology is the gas washout vent, wherein the first and/or second openings have a varying cross sectional area with a minimum cross sectional area that is larger than a cross sectional area of the constricted passage. The minimum cross sectional area of each opening may be taken at the narrowest point of each opening and compared to the cross sectional area of the constricted passage between the first and second openings. The minimum cross sectional area of each opening may be between 0.3 to 1 mm2. Preferably, the minimum cross sectional may be 0.5 mm2. In contrast, the cross sectional area of the constricted passage may be between 0.05 to 0.2 mm2. Preferably, the cross sectional area of the constricted passage may be 0.1 mm2. A varying cross sectional area of the openings may provide desired varying flow characteristics of exhaled gases through the first and/or second openings. The walls of each opening may be structured to provide the varying cross sectional such that the flow of exhaled gas is directed to provide the desired flow characteristics. For example, the openings may be formed by a curved and/or tilted wall to form the varying cross sectional area. Alternatively, the varying cross sectional area may be formed by a plurality of curved and/or tilted walls. The at least one wall forming the openings may provide a tortuous flow path for the flow of exhaled gases flowing through the openings. Moreover, the at least one wall may be angled to direct the flow in a desired orientation. Similarly, the walls of the first and/or second openings may converge towards the constricted passage. In an alternative example, the first openings may be angled relative to the second openings to provide the tortuous flow path through the vent. The at least one wall of the first and second openings may direct the flow of exhaled gases in manner to reduce noise and increase diffuseness.

Another aspect of one form of the present technology is the gas washout vent, wherein the first and/or second openings are symmetrical, each having a central axis. The plurality of first openings may have parallel central axes. The plurality of second openings may also have parallel central axes. Each vent hole may comprise a first opening having a central axis that is angled relative to the central axis of the corresponding second opening to define a tortuous flow path of exhaled gas through the vent hole. The plurality of first openings may be offset from the plurality of second openings such that the openings partially overlap to form the constricted passage. Alternatively, two or more of the plurality of first openings may have a central axis that is angled differently to one another to increase the diffuseness of the vent flow. Similarly, two or more of the plurality of second openings may also have a central axis that is angled differently to one another to increase the diffuseness of the vent flow.

Another aspect of one form of the present technology is the gas washout vent, wherein the first and/or second openings are asymmetrical. The first openings may be offset from the second openings such that they only partially overlap to form the constricted passage. The asymmetrical shapes of the openings may decrease noise of the vent flow and/or increase its diffuseness.

Another aspect of one form of the present technology is the gas washout vent, wherein the first and second sides are integrally formed. The first and second sides may be moulded into a single piece, having a plurality of first openings on the first side that partially overlap corresponding second openings on the second side to form a constricted passage therebetween. Integrally forming the vent allows for an easy way to manufacture a vent having smaller vent holes at the constricted vent passage formed from partially overlapping larger vent openings on each side of the vent. Alternatively, the first side may be separately formed from the second side of the vent. The first side may be permanently or semi-permanently attached to the second side. In another example, the first side may be removably attached to the second side.

Another aspect of one form of the present technology is a patient interface for sealed delivery of a flow of air at a continuously positive pressure with respect to ambient air pressure to an entrance to the patient's airways including at least entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing; said patient interface comprising a gas washout vent. The gas washout vent may be configured to allow a flow of patient exhaled gas to an exterior of the patient interface to minimise rebreathing of exhaled gas by the patient. The vent may comprise a plurality of vent passages extending between a first and second side of the vent. Each vent passage comprising a first opening extending from the first side towards the second side and a second opening extending from the second side towards the first side. The first and second openings only partially overlap each other along a plane to form constricted passages therebetween, the plane lying between the first and second sides. The patient interface may comprise a shell forming a plenum chamber for the delivery of therapy pressure to the entrance of the patient's airways. The vent may be integrally formed with the vent. Alternatively the vent may be removably attachable to the patient interface. For example, the vent may be removably attached to the shell of the patient interface. The patient interface may further comprise a connecting member such as an elbow connector for fluidly connecting the patient interface to a gas delivery conduit. The vent may be removably attached or integrally formed with the connecting member or gas delivery conduit. The vent may be orientated such that the second side of the vent is facing an interior or plenum chamber of the patient interface.

An aspect of one form of the present technology is a method of manufacturing a gas washout vent for a patient interface, the vent configured to allow a flow of patient exhaled gas to an exterior of the patient interface to minimise rebreathing of exhaled gas by the patient, said vent comprising a plurality of vent passages extending from a first side to a second side. The gas washout vent may be manufactured by the process comprising the steps of providing a moulding tool comprising a first plurality of pins to extending from a first side towards a second side of the tool and a second plurality of pins extending from the second side towards the first side. The first plurality of pins and the second plurality of pins may slidingly extend towards each other. Alternatively either of the first of pins or the second plurality of pins may slidingly extend. A cavity is formed around the first and second plurality of pins for moulding respective first and second openings. The pins are positioned such that the first plurality of pins engage the second plurality of pins on opposing ends between the first and second sides of the tool. The first plurality of pins are offset from the second plurality of pins to only partially overlap upon engagement. The first plurality of pins may be axially offset to the second plurality of pins according to an axis of symmetry of each pin. Each pin of the first plurality of pins may engage one or more pins of the second plurality of pins, such that a constricted vent passage may be moulded around the point of engagement. All the pins may engage on a single horizontal plane that runs between the first and second sides of the moulding vent. The pins may then be retracted towards opposing sides to demould the tool from the vent. The first plurality of pins may be offset from the second plurality of pins such that only a portion of the end of each first plurality of pins engages with only a portion of the end of each second plurality of pins. This engaging portion provides the partial overlap such that moulding around the engaging ends forms a constricted passage between the first and second openings. Moulding a gas washout vent using this method allows for the moulding of gas washout vents with smaller vent holes provided by the constricted passages without the need for a tool with smaller moulding pins. The probability of breakage after short term use is increased when moulding pins are made smaller and thinner for moulding corresponding small vent holes around the pins. This ultimately reduces the reliability and robustness of the moulding tool for prolonged use. Thus, a moulding tool with opposing pins on a first and second side may provide a means for moulding smaller vent holes without the need for smaller or thinner pins. The first and/or second plurality of pins may each have a cross section area of between 0.3 to 1 mm$^2$. The cross sectional area of each of the first and/or second plurality of pins may be 0.5 mm$^2$. The first plurality of pins may partially overlap the second plurality of pins such that they engage across a cross sectional area of between 0.05 to 0.2 mm$^2$. The partial overlap may form a constricted passage with a cross sectional area of between 0.05 to 0.2 mm$^2$. The constricted passage may have a cross sectional area of 0.1 mm$^2$. Having the first and second plurality of pins engage in this manner also allows for ease of moulding vent holes with constricted passages that are or irregular shapes to increase diffusivity and/or decrease noise by providing a tortuous flow path for exhaled gases through the vent. The irregularly shaped vent holes may be formed by the first and/or second plurality of pins with irregular shapes. Having the pins engage on opposing sides allows for easier retraction of the pins towards their respective sides after moulding the vent holes.

An aspect of the present technology is directed to a gas washout vent for a patient interface, the vent configured to allow a flow of patient exhaled gas to an exterior of the patient interface to minimise rebreathing of exhaled gas by the patient. The gas washout vent may comprise: a plurality of vent passages extending between a first and a second side of the vent, each vent passage comprising: a plurality of first openings extending from the first side towards the second side, said first openings being uniform in size and shape; a plurality of second openings extending from the second side towards the first side, said second openings being uniform in size and shape; and wherein the first openings and the second openings partially overlap each other at an interface to form constricted passages therebetween.

In examples, (a) the first openings and the second openings may terminate at the interface to form the constricted passages, (b) the interface may be curved, (c) the interface may be flat, (d) each of the first openings may partially overlap a plurality of the second openings, (e) each of the first openings may have a substantially constant cross sectional area through the first side that is larger than a cross sectional area of the constricted passage, (f) each of the second openings may have a substantially constant cross sectional area through the second side that is larger than a cross sectional area of the constricted passage, (g) each of the first openings and each of the second openings may be formed by a curved wall, (h) the wall may form a cylindrical opening, (i) at least one of the first openings and at least one of the second openings may have a varying cross sectional area, (j) the varying cross sectional area may have a minimum cross sectional area that is larger than the cross sectional area of the corresponding constricted passage, (k) each of the first openings may be formed by at least a first wall, (l) the first wall may comprise a plurality of first sides, (m) the plurality of first sides may include at least one tilted first side to form an angled flow path through each of the first openings, (n) the plurality of first sides may include at least one curved first side, (o) each of the second openings may be formed by a second wall, (p) the second wall may comprise a plurality of second sides, (q) the plurality of second sides may include at least one tilted second side to form an angled flow path though each of the second openings, (r) at least one of the second sides of the second wall of one of the second openings may be tilted relative to at least one of the second sides of the second wall of an adjacent one of the second openings such that the flow of exhaled gases exiting one of the second openings is directed towards the flow exiting the adjacent one of the second openings, (s) the plurality of second sides may include at least one curved second side, (t) the cross-sectional area of each of the first openings may decrease towards the constricted passage, (u) the cross-sectional area of each of the second openings may decrease towards the constricted passage, (v) each of the constricted passages has a cross sectional area between 0.05 mm2 and 0.2 mm2, (w) each of the constricted passages has a cross sectional area of 0.1 mm2, (x) each of the first openings may have a cross sectional area between 0.3 mm2 and 1 mm2, (y) each of the first openings may have a cross sectional area of 0.5 mm2, (z) each of the second openings may have a cross sectional area between 0.3 mm2 and 1 mm2, (aa) each of the second openings may have a cross sectional area of 0.5 mm2, (bb) an axis may be defined through each of the first openings and each of the second openings, (cc) each axis defined through each of the first openings may be oriented relative to the interface at a different angle than each axis defined through each of the second openings, (dd) the axes defined through each of the first openings may be parallel, (ee) the axes defined through each of the second openings may be parallel, (ee) each of the first openings may be a cube or a cuboid in shape, (ff) each of the second openings may be a cube or a cuboid in shape, (gg) each of the first openings may be asymmetrical about an axis, (hh) each of the second openings may be asymmetrical about an axis, and/or (ii) the first side and the second side may be integrally formed.

An aspect of the present technology is directed to a patient interface for sealed delivery of a flow of air at a continuously positive pressure with respect to ambient air pressure to an entrance to the patient's airways including at least entrance of the patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The patient interface may comprise: a gas washout vent configured to allow a flow of patient exhaled gas to an exterior of the patient interface to minimise rebreathing of exhaled gas by the patient, said vent comprising: a plurality of vent passages extending between a first side and a second side of the gas washout vent, each vent passage comprising: a first opening extending from the first side towards the second side and being uniform in size and shape; a second opening extending from the second side towards the first side and being uniform in size and shape; and wherein the first openings and the second openings partially overlap each other along an interface to form constricted passages therebetween.

In examples, (a) the interface may be curved, (b) the interface may be flat, (c) the patient interface may further comprise a plenum chamber that at least in part defines a breathing chamber of the patient interface, (d) the gas washout vent may be integrally formed with the plenum chamber, (e) the gas washout vent may be removably attached to plenum chamber, (f) the second side of the gas washout vent may face the breathing chamber of the patient interface, (g) the patient interface may further comprise a connecting member configured to connect the patient interface to a gas delivery conduit, the gas washout vent provided to the connecting member, (h) the second side of the gas washout vent may face an interior of the connecting member, (i) the gas washout vent may be integrally formed with the connecting member, and/or (j) the gas washout vent may be removably attached to the connecting member.

An aspect of the present technology is directed to a method of manufacturing a gas washout vent for a patient interface, the vent configured to allow a flow of patient exhaled gas to an exterior of the patient interface to minimise rebreathing of exhaled gas by the patient, said vent comprising a plurality of vent passages extending from a first side to a second side. The method may comprise: providing a moulding tool comprising: a first plurality of pins extending from a first side towards a second side of the tool; a second plurality of pins extending from the second side towards the first side of the tool; and a cavity formed around the first plurality of pins and the second plurality of pins; wherein the first plurality of pins and the second plurality of pins extend to engage on opposing ends between the first side and the second side such that the first plurality of pins are offset from the second plurality of pins to partially overlap upon engagement; and adding molten moulding material to the cavity of the moulding tool such that a plurality of first openings and a plurality of second openings that are partially overlapping are moulded around the first plurality of pins and the second plurality of pins to form constricted passages between the first openings and the second openings, the constricted passages formed around the engaging ends of the first plurality of openings and the second plurality of openings.

In examples, (a) the method may further comprise retracting the first plurality of pins and/or the second plurality of pins from the moulding material to demould the vent from the tool, (b) the pins may slidingly extend towards each other, (c) each of the first plurality of pins may engage with two or more of the second plurality of pins, (d) the first plurality of pins may engage with the second plurality of pins on opposing sides of a horizontal plane running through a point of engagement between the first plurality of pins and the second plurality of pins, (e) the first plurality of pins may have an axis of symmetry that is axially offset from an axis of symmetry of the second plurality of pins, (f) each of the first plurality of pins may have a cross sectional area between 0.3 mm2 and 1 mm2, (g) each of the first plurality of pins may have a cross sectional area of 0.5 mm2, (h) the first plurality of pins may partially overlap the second plurality of pins to form each of the constricted passages with a cross sectional area between 0.05 mm2 and 0.2 mm2, and/or (i) the cross sectional area of each of the constricted passages may be 0.1 mm2.

An aspect of the present technology is directed to a gas washout vent for a patient interface, the vent configured to allow a flow of patient exhaled gas to an exterior of the patient interface to minimise rebreathing of exhaled gas by the patient. The vent may comprise: a plurality of layers, wherein each layer comprises a plurality of vent passages extending between a first side and a second side of each layer, each vent passage comprising: a first opening extending from the first side towards the second side and being uniform in shape and size; a second opening extending from the second side towards the first side and being uniform in shape and size; and wherein each first opening and each second opening only partially overlap each other along an interface to form constricted passages therebetween.

An aspect of the present technology is directed to a gas washout vent for a patient interface, the vent configured to allow a flow of patient exhaled gas to an exterior of the patient interface to minimise rebreathing of exhaled gas by the patient. The vent may comprise: a plurality of vent passages extending between a first side and a second side of the vent, each vent passage comprising: a first opening extending from the first side towards the second side and being uniform in shape and size; a second opening extending from the second side towards the first side and being uniform in shape and size; and wherein each first opening is offset from each second opening along an interface to form a constricted passage therebetween.

An aspect of the present technology is directed to a gas washout vent for a patient interface, the vent configured to allow a flow of patient exhaled gas to an exterior of the patient interface to minimise rebreathing of exhaled gas by the patient. The vent may comprise: a plurality of vent passages formed by a wall extending between a first side and a second side of the vent, each vent passage comprising: a first opening formed by the wall extending from the first side towards the second side and being uniform in shape and size; a second opening formed by the wall extending from the second side towards the first side and being uniform in shape and size; and wherein the wall transitions between the first opening to the second opening by a stepped cross section to form a constricted passage therebetween.

An aspect of the present technology is directed to a vent for a patient interface. The vent may comprise: a first side having a plurality of first openings defined by a plurality of first walls, said first openings being uniform in size and shape; a second side having a plurality of second openings defined by a plurality of second walls, said second openings being uniform in size and shape, wherein the first side and the second side are positioned adjacent to one another at an interface region, and wherein each of the first openings overlaps with at least two of the second openings at the interface region and each of the second openings overlaps with at least two of the first openings at the interface region such that a constricted passage is formed at each overlap of one of the first openings and one of the second openings.

In examples, (a) each of the first openings may be defined by at least one side of the first walls and each of the second openings is defined by at least one side of the second walls, (b) each first opening may be defined by a plurality of sides of the first walls and each second opening is defined by a plurality of sides of the second walls, (c) each first opening may have a substantially polygonal profile and each second opening has a substantially polygonal profile, (d) the first walls may be comprised of a first plurality of ellipsoidal structures and the second walls may be comprised of a second plurality of ellipsoidal structures, (e) the first plurality of ellipsoidal structures may be uniform and overlapping, (f) the second plurality of ellipsoidal structures may be uniform and overlapping, (g) the first plurality of ellipsoidal structures and the second plurality of ellipsoidal structures may be identical in shape and size, (h) the first plurality of ellipsoidal structures and the second plurality of ellipsoidal structures may be different in shape and size, (i) the sides of each of the first walls may be tilted toward one another relative to the interface region and the sides of each of the second walls may be tilted toward one another relative to the interface region, (j) the sides of each of the first walls may be tilted in the same direction relative to the interface region and the sides of each of the second walls may be tilted toward one another relative to the interface region, (k) the sides of each of the first walls may be tilted in the same direction relative to the interface region, the sides of each of the second walls may be tilted in the same direction relative to the interface region, and the sides of the first walls and the sides of the second walls may be tilted in opposite direction relative to one another, (l) each first opening may be defined by a single side of the first walls such that each first opening has a profile that is substantially elliptical or substantially circular, (m) each second opening may be defined by a single side of the second walls such that each second opening has a profile that is substantially elliptical or substantially circular, (n) the first walls and/or the second walls may be curved, (o) each of the first openings may overlap with four of the second openings and each of the second openings may overlap with four of the first openings, (p) the first walls and the second walls may overlap, (q) the first side and the second side may be spaced apart at the interface region, (r) the first side and the second side may be in contact at the interface region, (s) the first side and the second side may comprise a single piece of homogeneous material, (t) the first side and the second side may comprise two separate pieces of homogeneous material that are permanently attached, (u) the first side and the second side may comprise two separate pieces of homogeneous material that are releasably attached, (v) the interface region may be planar such that the first side and the second side are substantially flat, (w) the interface region may be curved in at least one direction such that the first side and the second are curved in said at least one direction, (x) the first openings may be distributed on the first side in any one of a rectangular grid pattern, a circular pattern, a spiral pattern, an elliptical pattern, a square pattern, a polygonal pattern, a series of rows and columns, and a pattern mirrored about an axis of the first side, (y) the second openings may be distributed on the second side in any one of a rectangular grid pattern, a circular pattern, a spiral pattern, an elliptical pattern, a square pattern, a polygonal pattern, a series of rows and columns, and a pattern mirrored about an axis of the second side, (z) each constricted passage may define a flow path for the flow of gas through corresponding ones of the first openings and corresponding ones of the second openings, (aa) the flow path may be any one of linear, non-linear, and tortuous, (bb) the first openings and the second openings may be sized and shaped such that at least two adjacent flow paths cross one another, and/or (cc) a patient interface for sealed delivery of a flow of air at a continuously positive pressure with respect to ambient air pressure to an entrance to the patient's airways including at least the entrance of the patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, said patient interface may comprise: a sealing structure configured to form a pneumatic seal around an area surrounding an entrance to the patient's airways; a positioning and stabilising structure configured to maintain the sealing structure in sealing contact with the area surrounding an entrance to the patient's airways while maintaining a therapeutic pressure at the entrance to the patient's airways; a plenum chamber configured to be pressurised at a pressure above ambient pressure in use; at least one vent according to any of the above examples, said vent being configured to allow a flow of patient exhaled CO2 to an exterior of the patient interface to minimise rebreathing of exhaled CO2 by the patient.

An aspect of the present technology is directed to a method of manufacturing a vent with a first tool having a first plurality of pins extending from a first base and a second tool having a second plurality of pins extending from a second base. The method may comprise: engaging the first tool and the second tool together such that the first plurality of pins and the second plurality of pins are in contact with one another at an interface region, the first plurality of pins at least partially defining a first plurality of voids and the second plurality of pins at least partially defining a second plurality of voids; molding the vent by filling the first plurality of voids and the second plurality of voids with a vent material; and disengaging the first tool and the second tool from one another after a predetermined period of time.

In examples, (a) the first plurality of pins and the second plurality of pins may be sized and shaped such that when engaged each of the first plurality of pins overlaps with at least two of the second plurality of pins and each of the second plurality of pins overlaps with at least two of the first plurality of pins, (b) each of the first plurality of voids may be defined at least in part by the first base, sides of the first plurality of pins, and a free end surface of one of the second plurality of pins and each of the second plurality of voids is defined at least in part by the second base, sides of the second plurality of pins, and a free end surface of one of the first plurality of pins.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
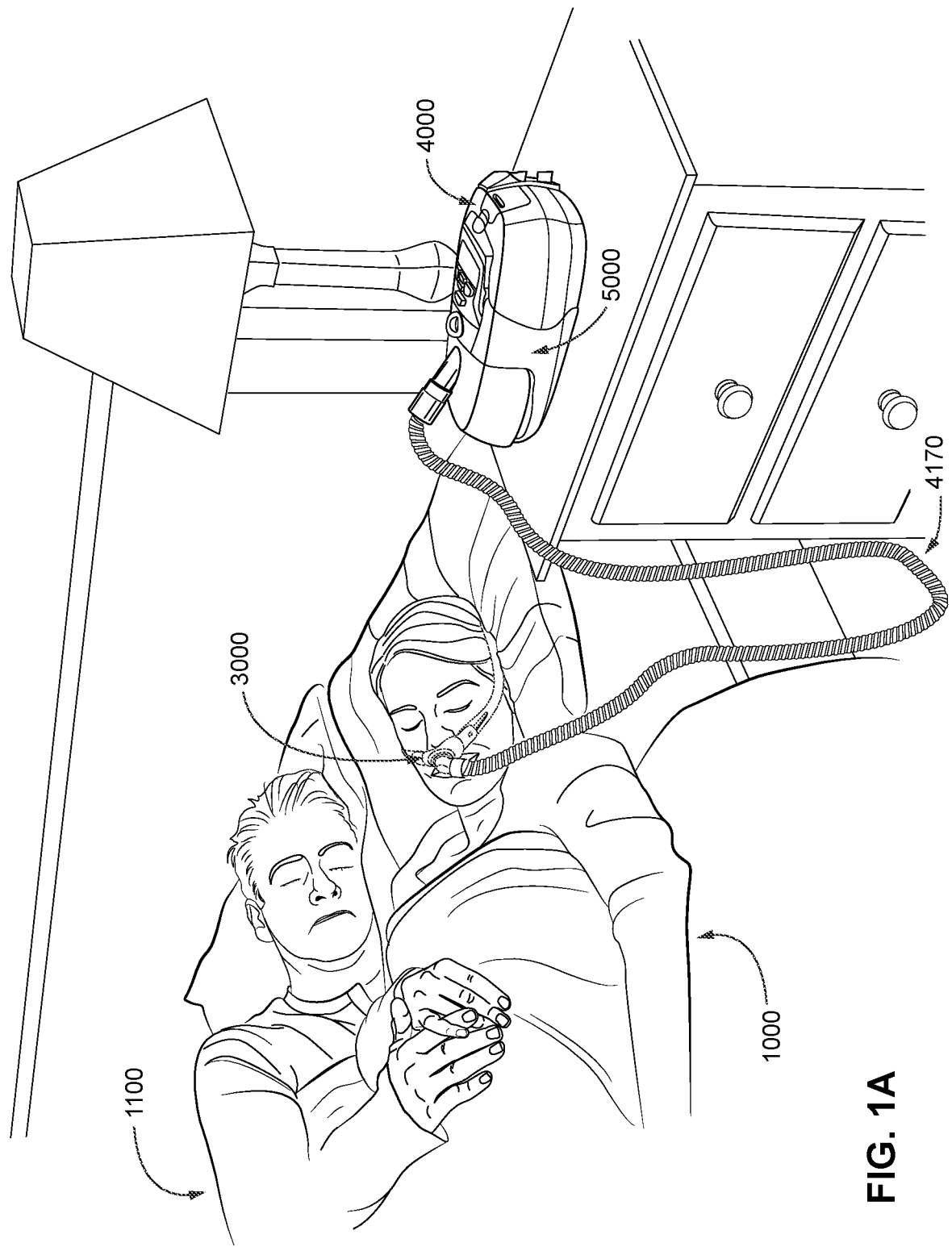
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
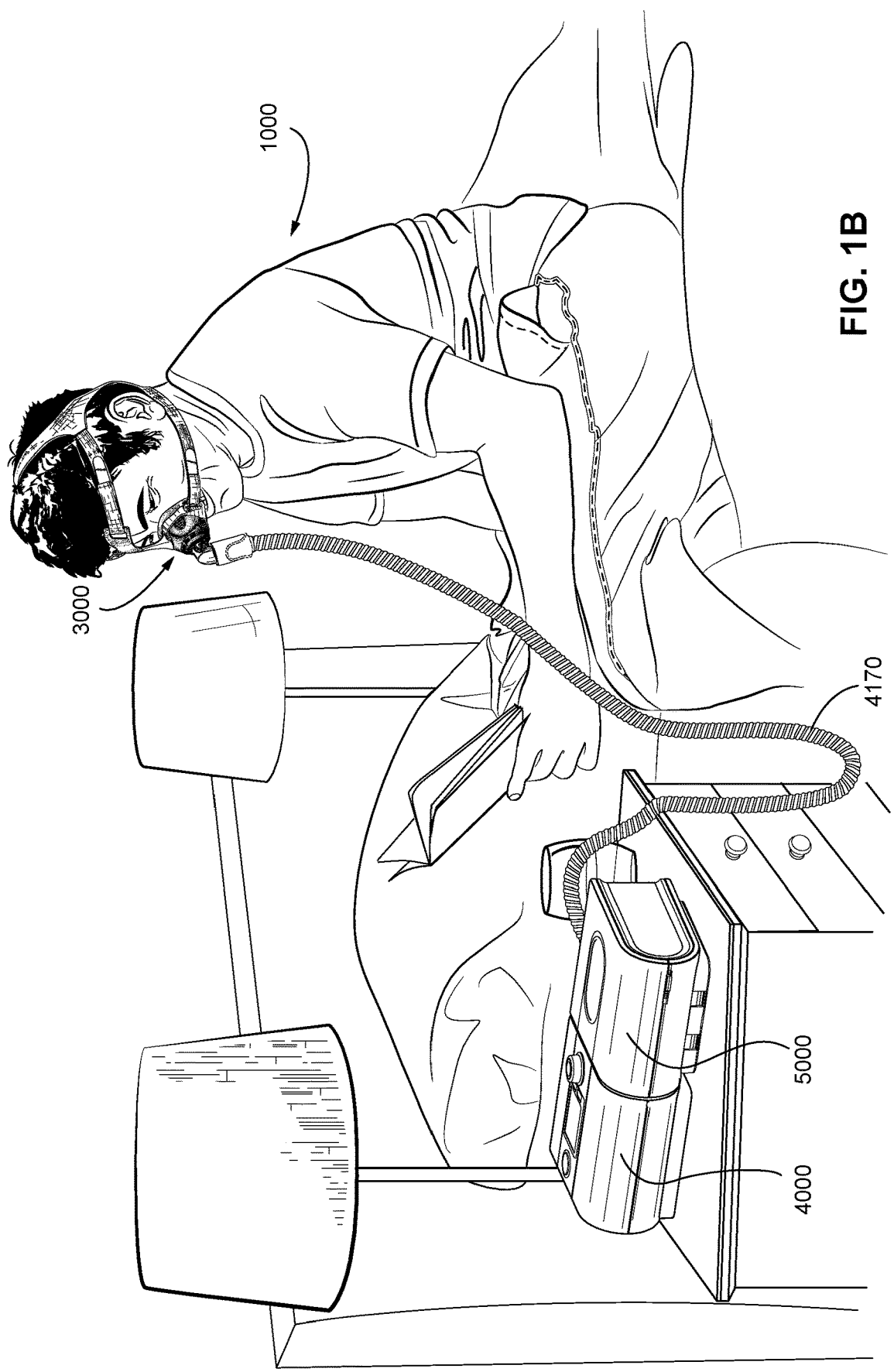
Figure 1C:
Figure 2A:
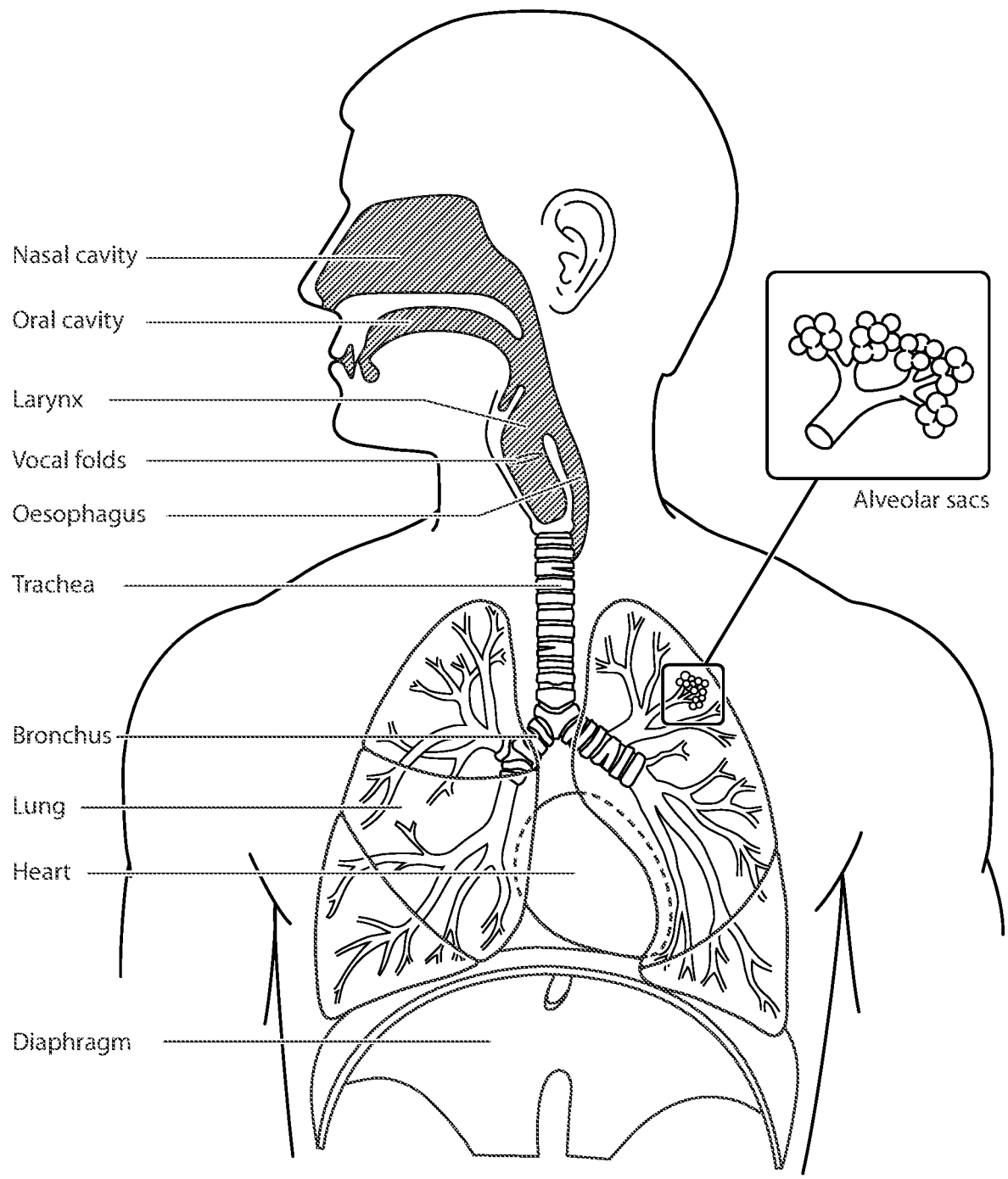

FIG. 2A shows an overview of a human respiratory system including the nasal and oral cavities, the larynx, vocal folds, oesophagus, trachea, bronchus, lung, alveolar sacs, heart and diaphragm.

Figure 2B:
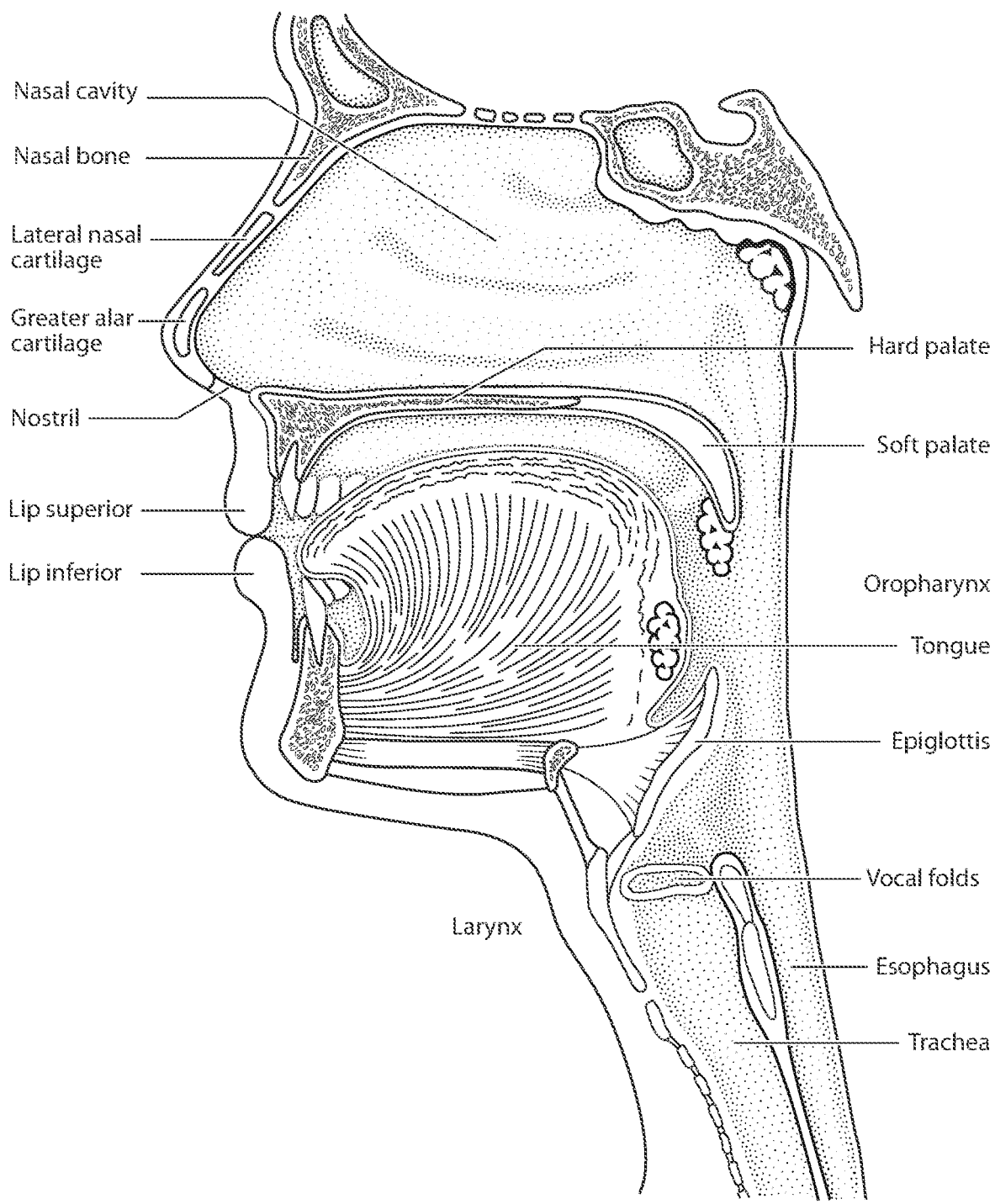

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
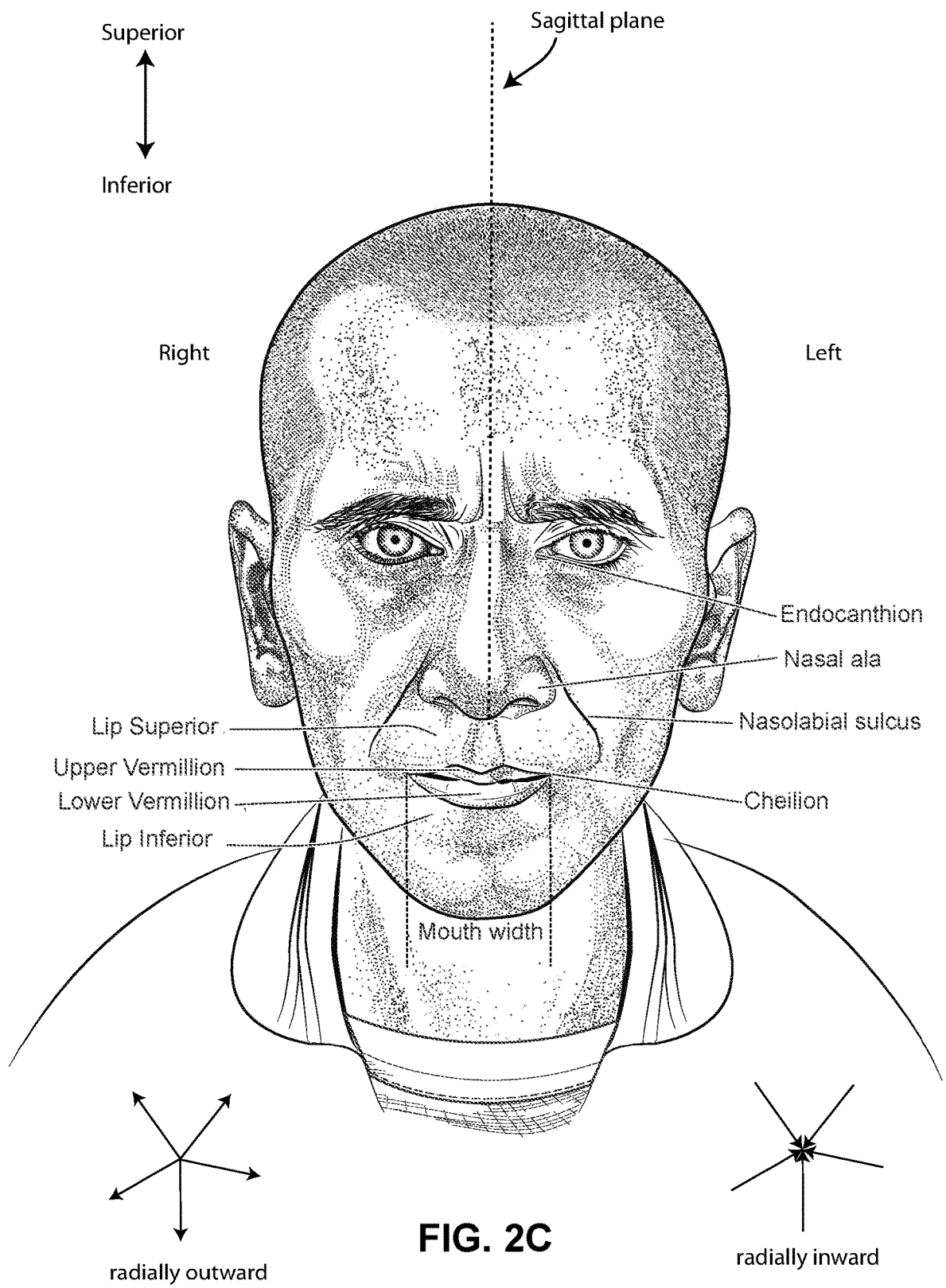

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
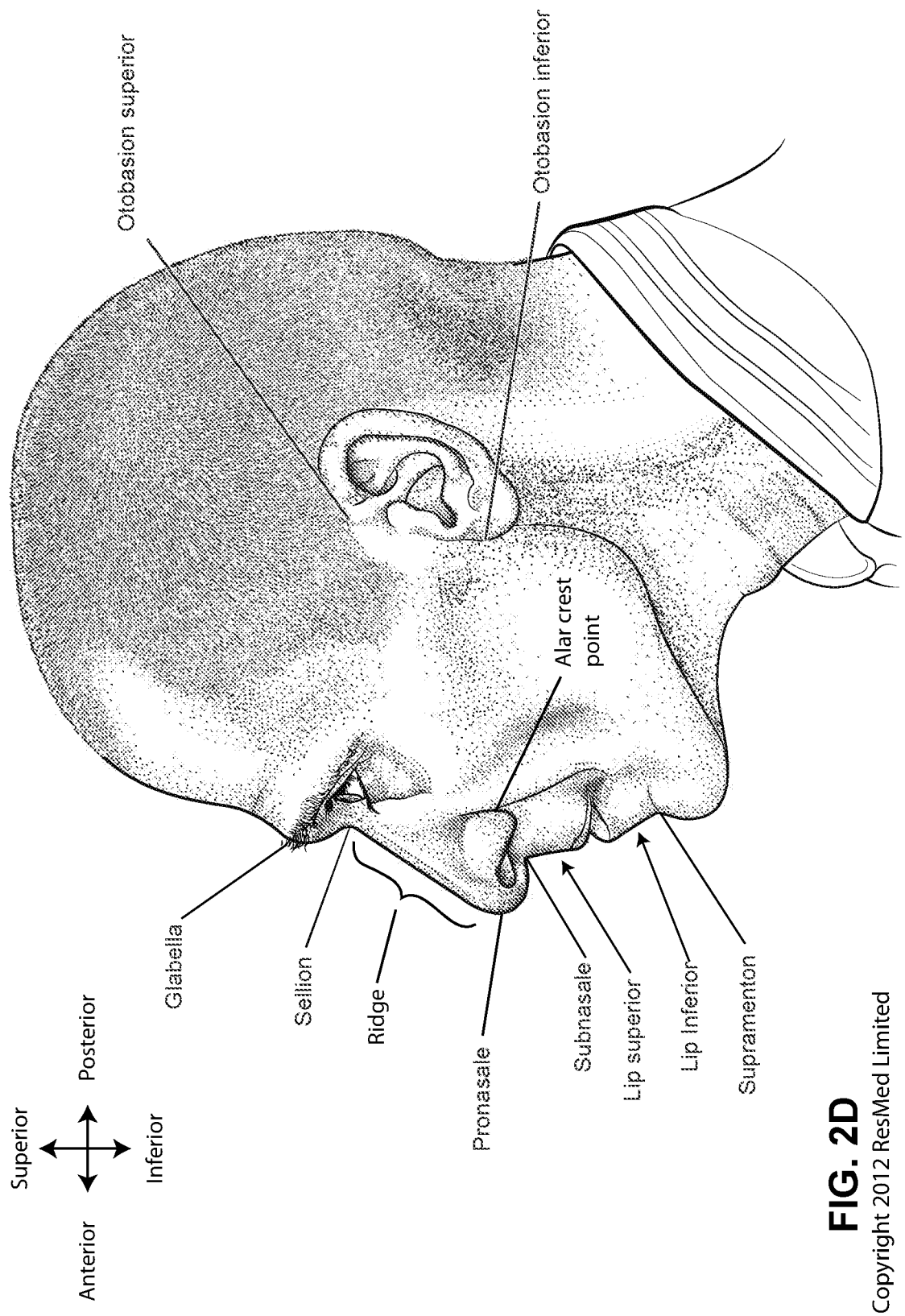

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
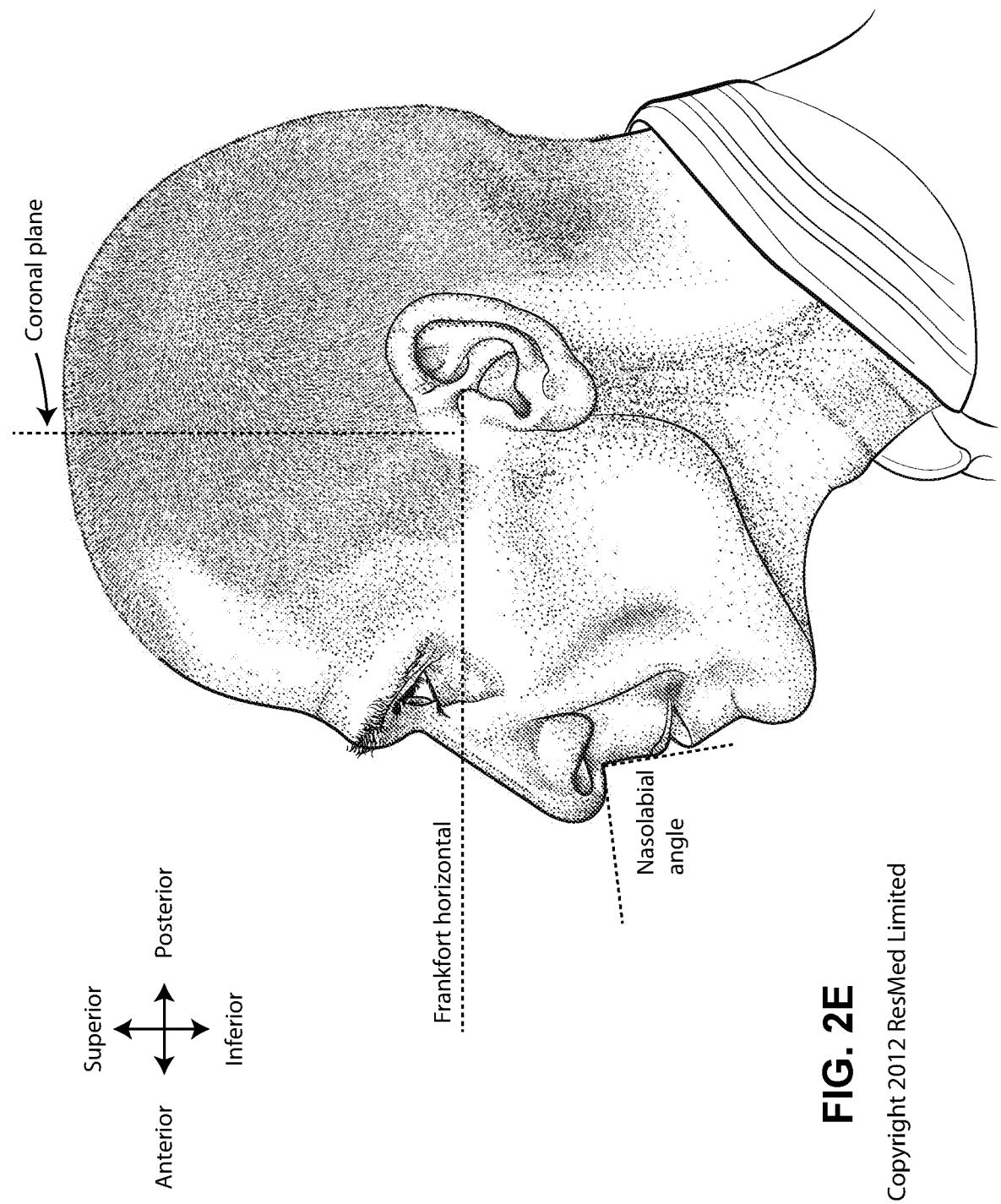

FIG. 2E is a further side view of a head. The approximate locations of the Frankfort horizontal and nasolabial angle are indicated. The coronal plane is also indicated.

Figure 2F:
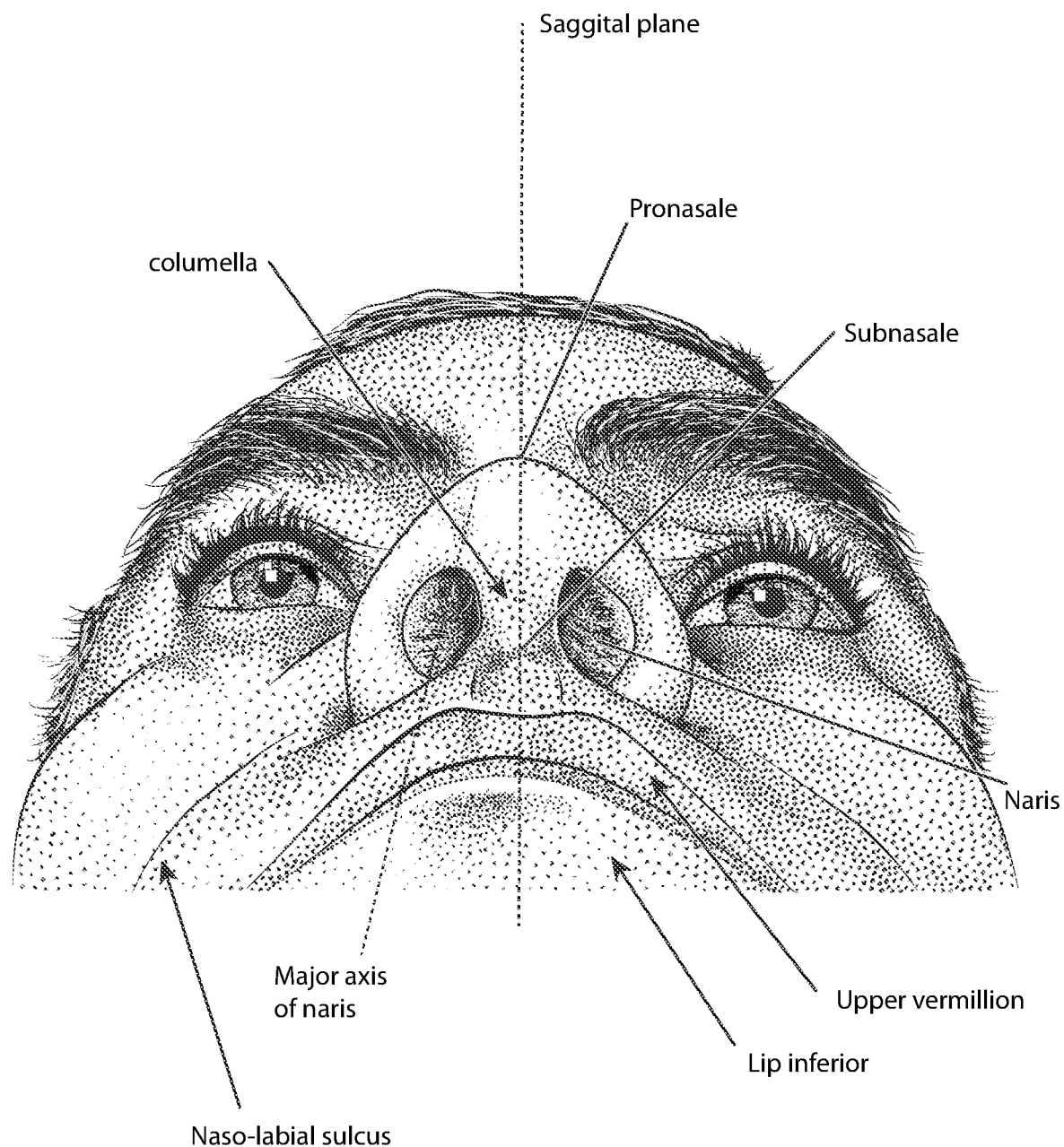

FIG. 2F shows a base view of a nose with several features identified including naso-labial sulcus, lip inferior, upper Vermilion, naris, subnasale, columella, pronasale, the major axis of a naris and the sagittal plane.

Figures 2G, 2H, 2I:
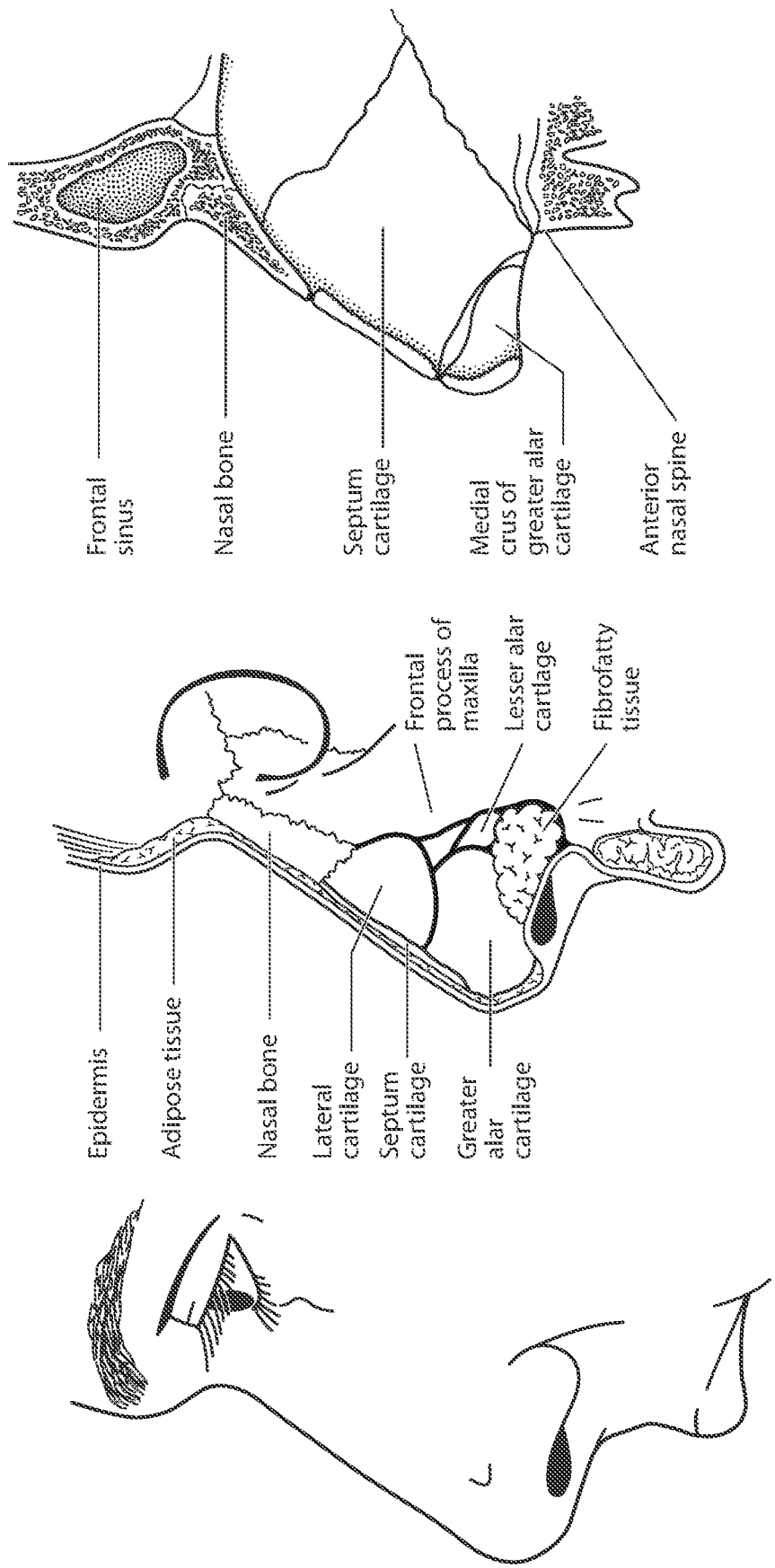

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
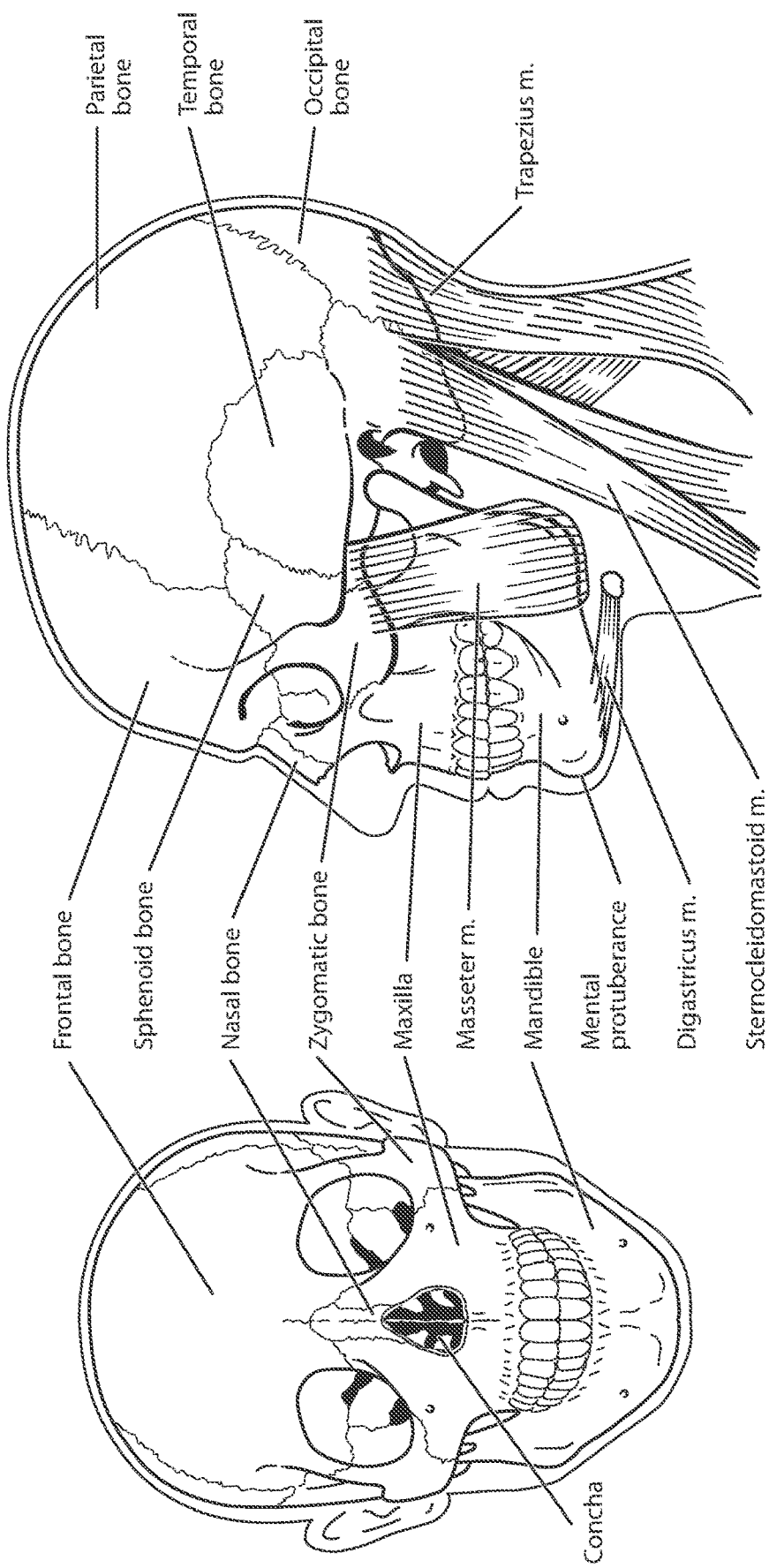

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
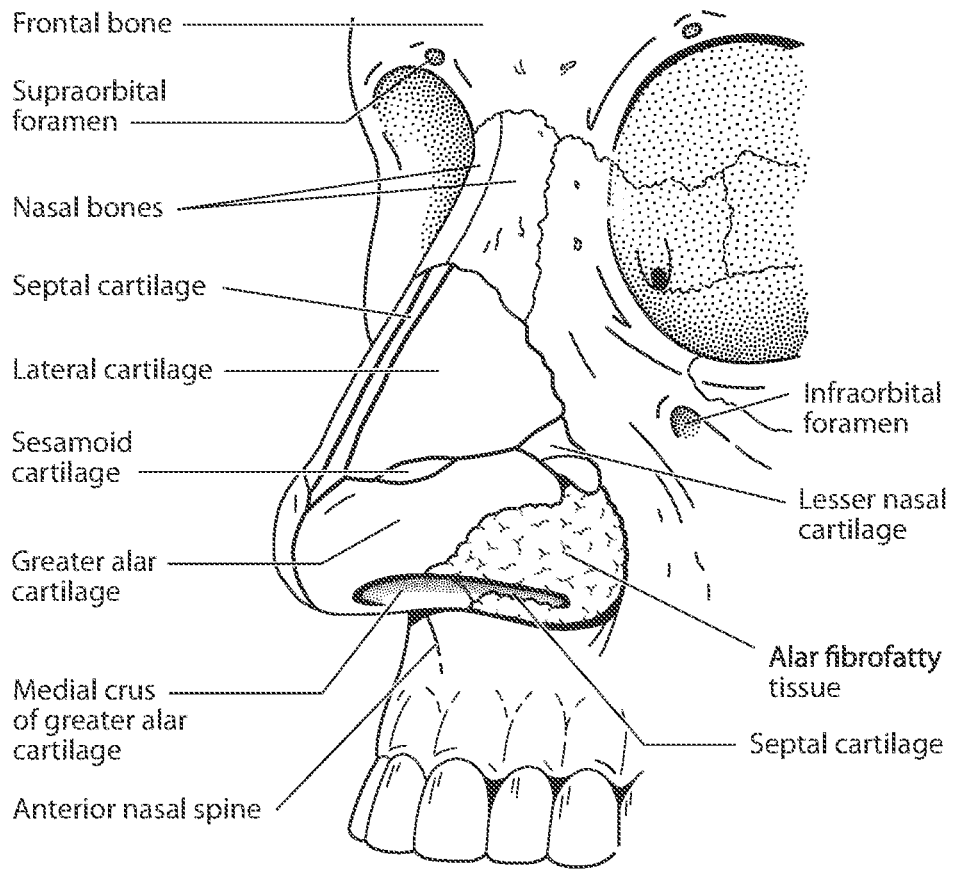

FIG. 2L shows an anterolateral view of a nose.

4.3 Patient Interface

Figure 3A:
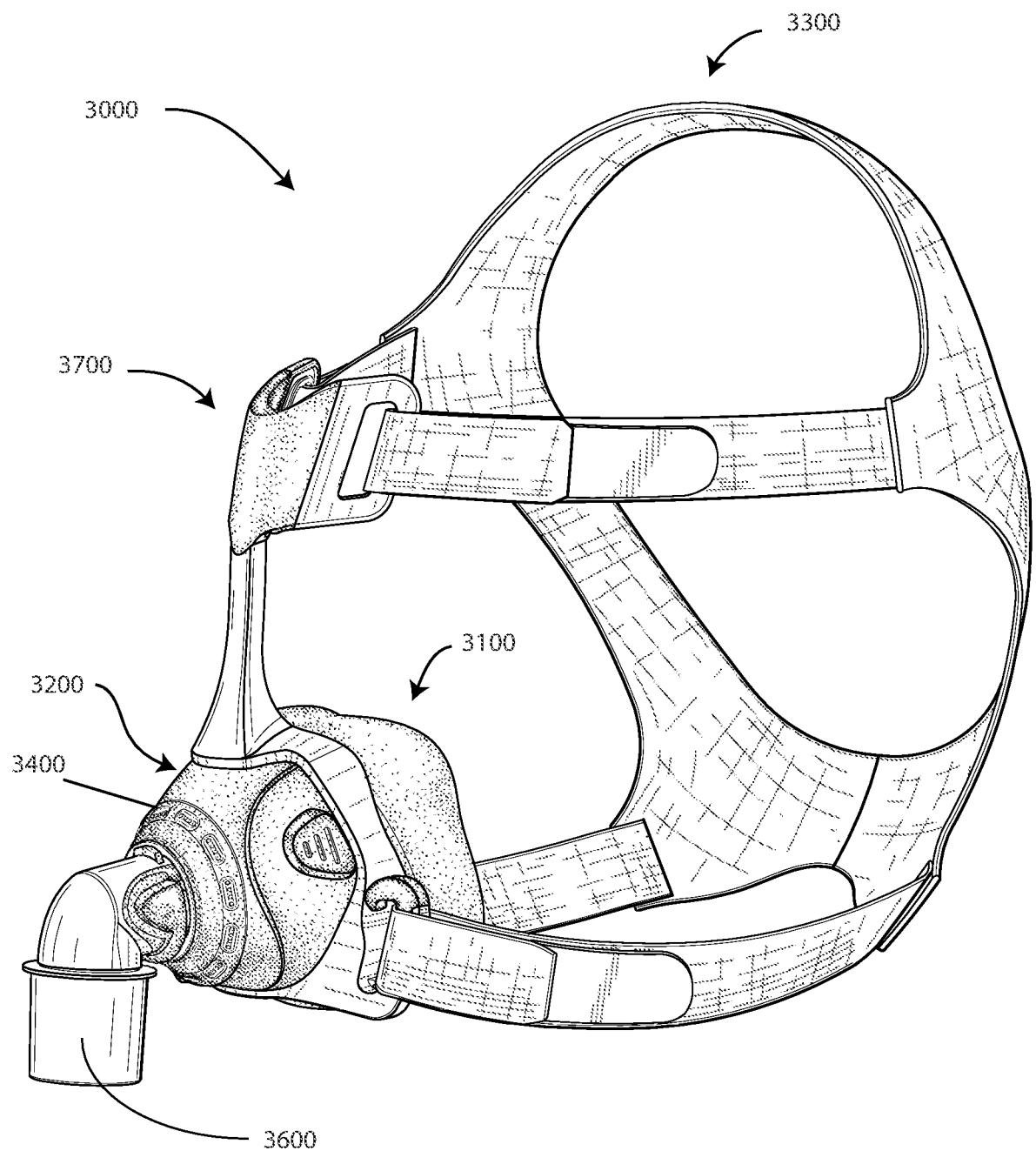

FIG. 3A shows a patient interface in the form of a nasal mask in accordance with one form of the present technology.

4.4 RPT Device

Figure 4A:
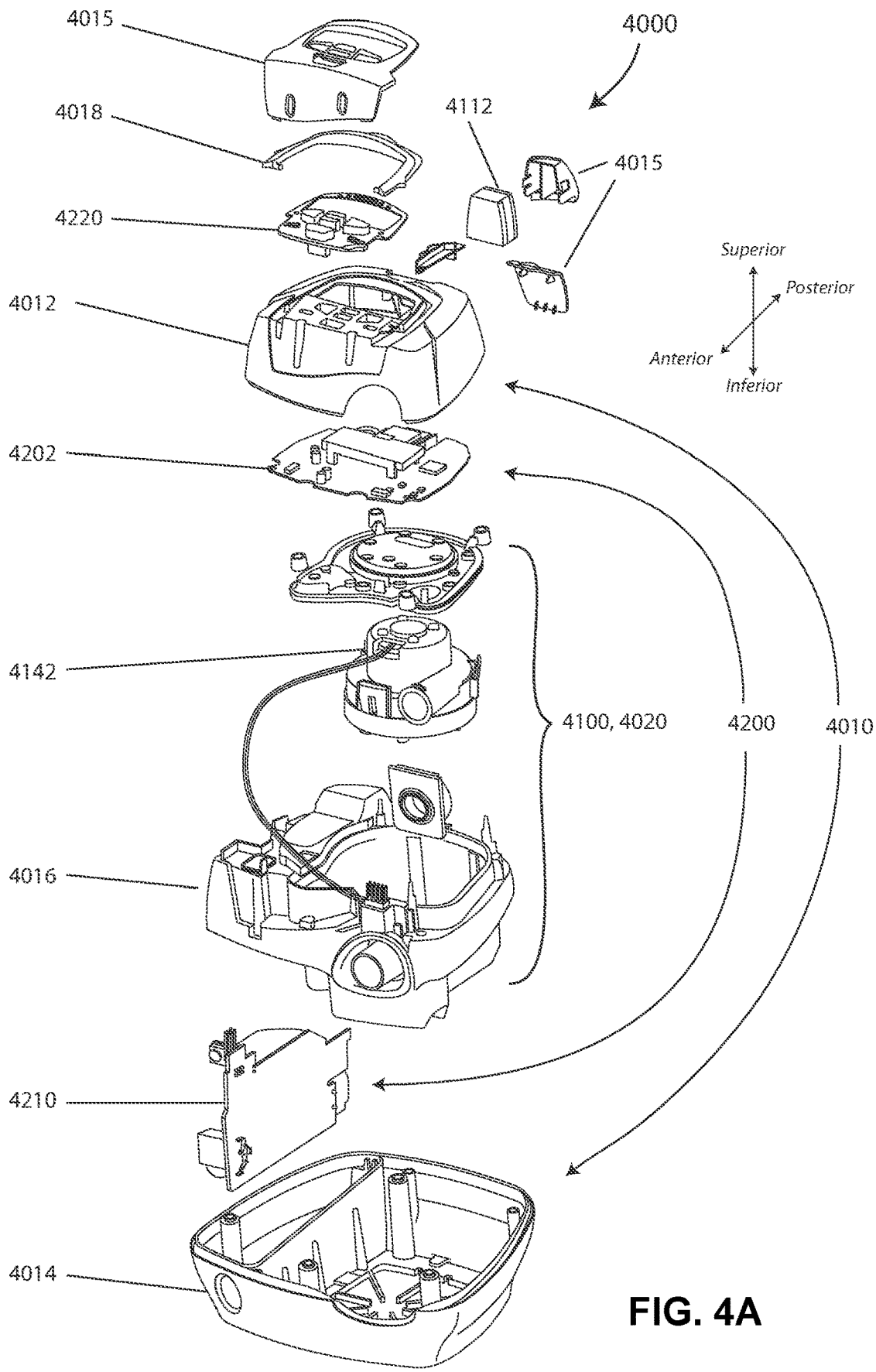

FIG. 4A shows an RPT device in accordance with one form of the present technology.

Figure 4B:
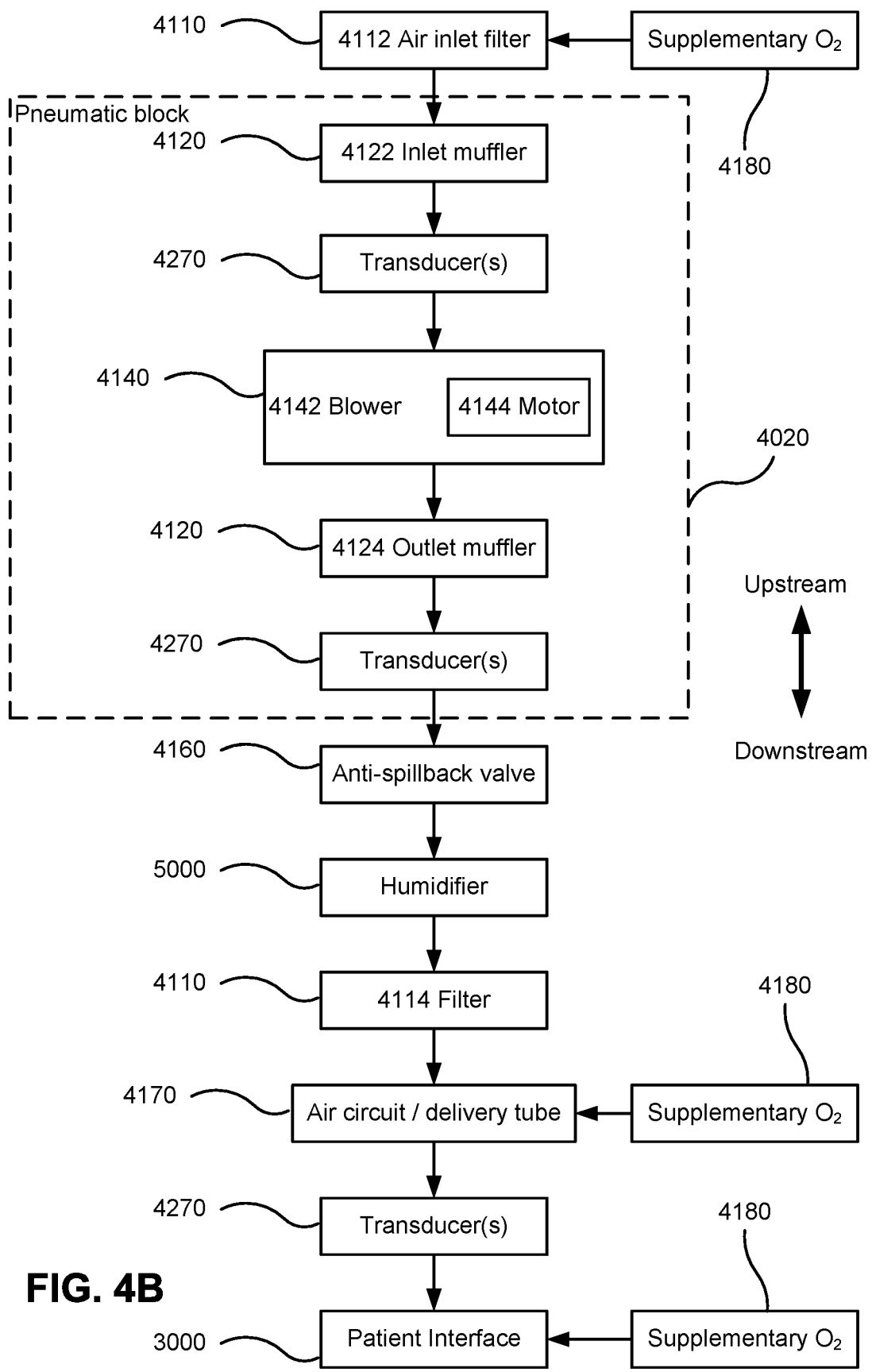

FIG. 4B is a schematic diagram of the pneumatic path of an RPT device in accordance with one form of the present technology. The directions of upstream and downstream are indicated.

4.5 Humidifier

Figure 5A:
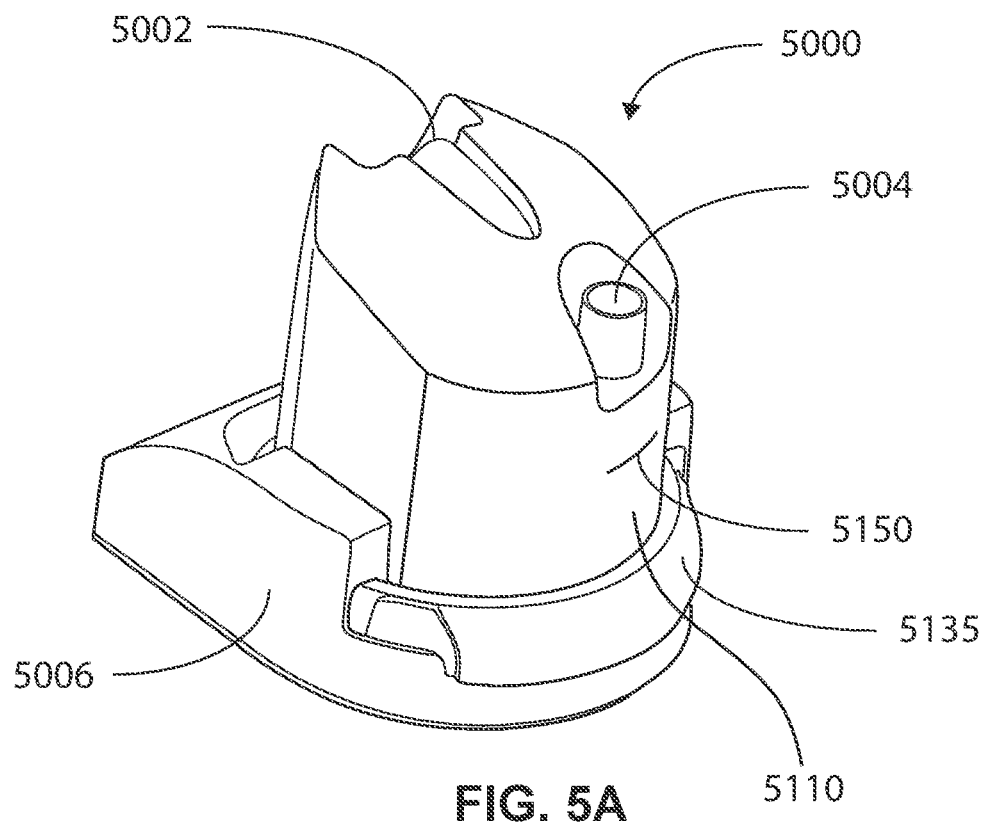

FIG. 5A shows an isometric view of a humidifier in accordance with one form of the present technology.

Figure 5B:
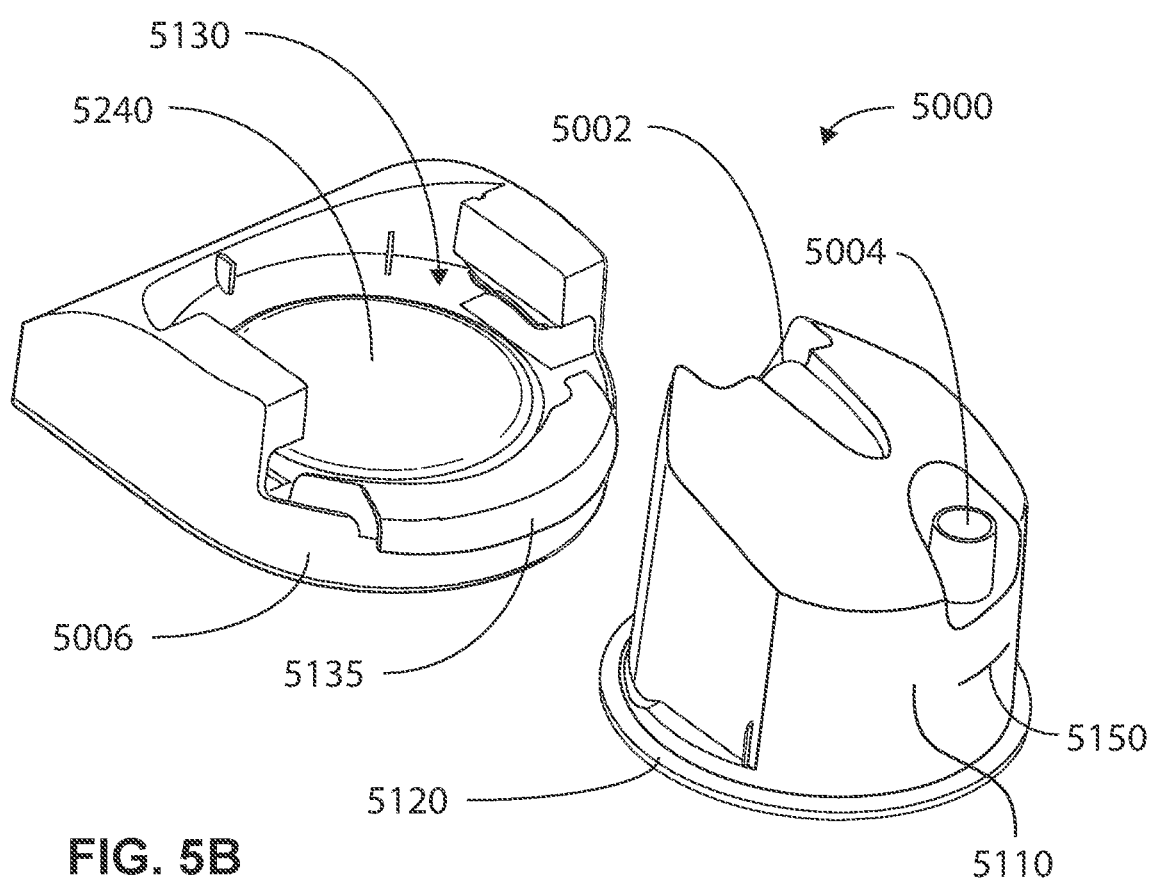

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
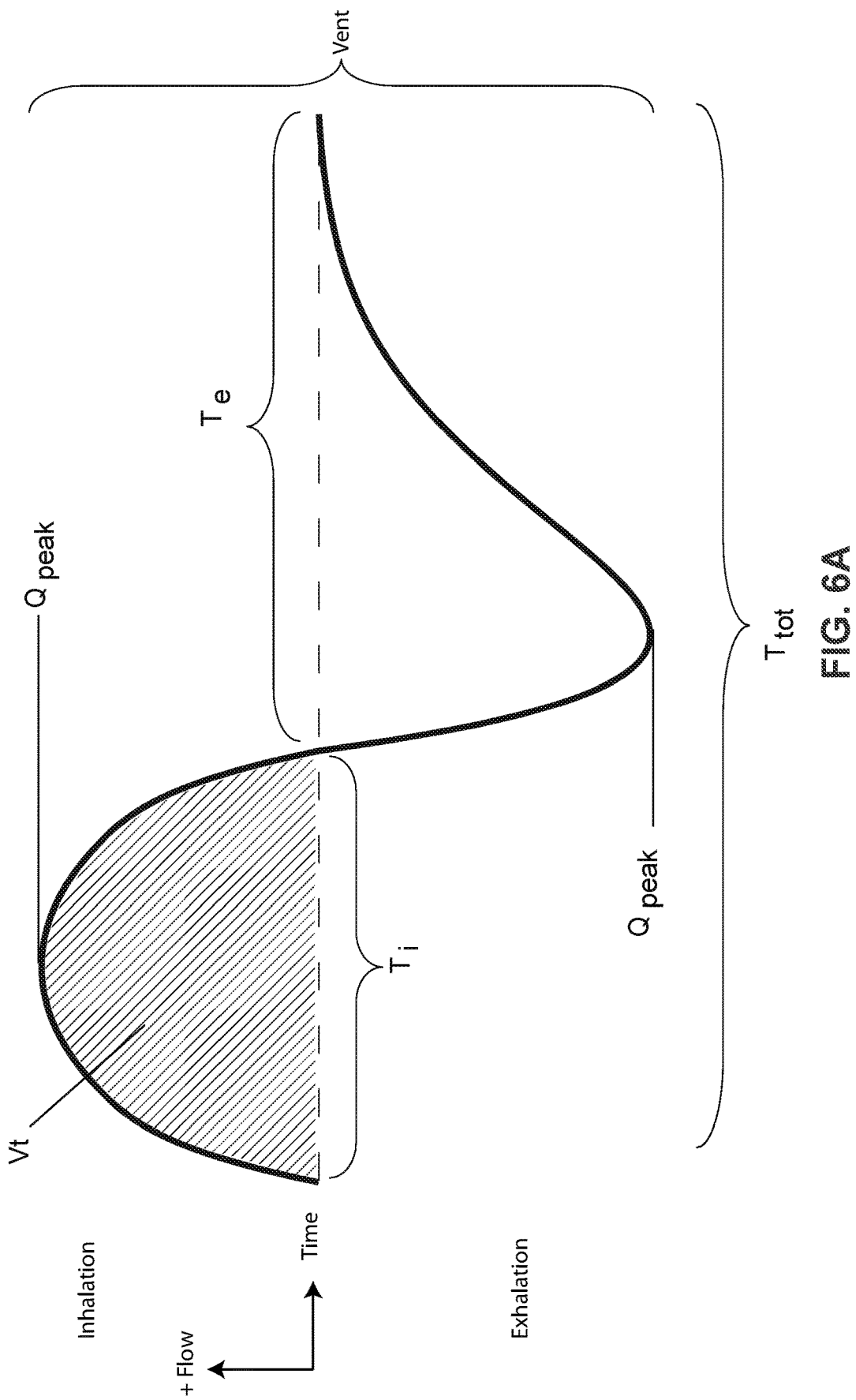

FIG. 6A shows a model typical breath waveform of a person while sleeping.

4.7 Vent

Figure 7A:
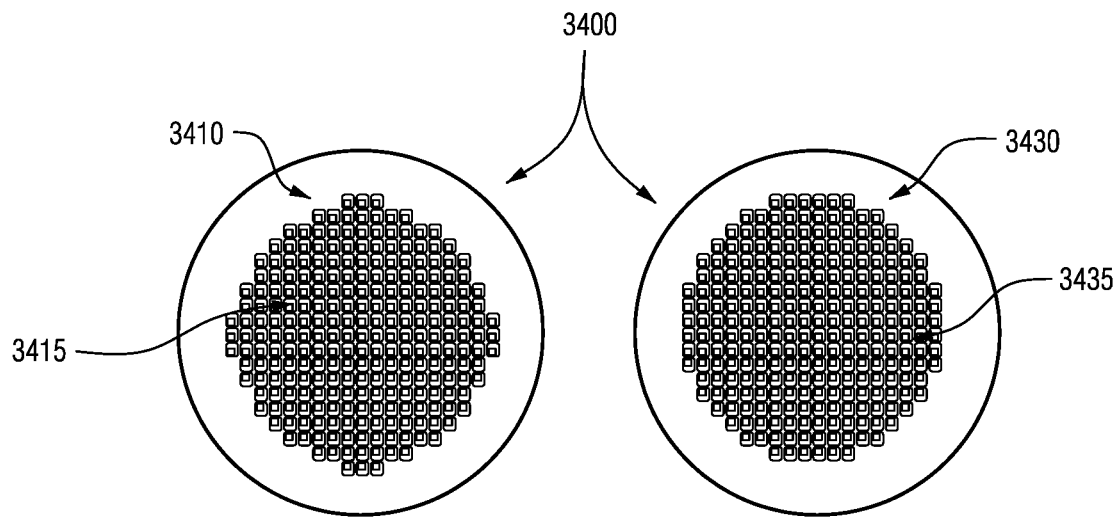

FIG. 7A shows a first side and second side of a vent in accordance with an example of the present technology.

Figure 7B:
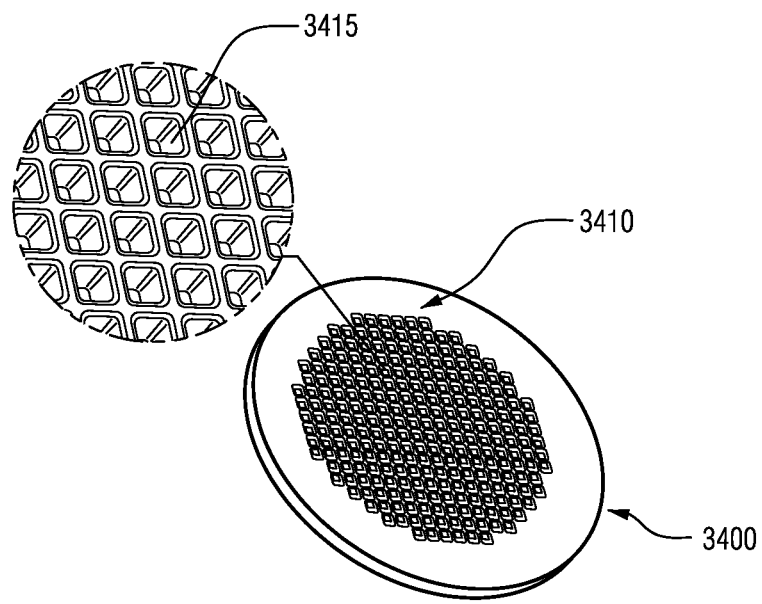

FIG. 7B shows a detailed perspective view of the first side of the vent shown in FIG. 7A.

Figure 7C:
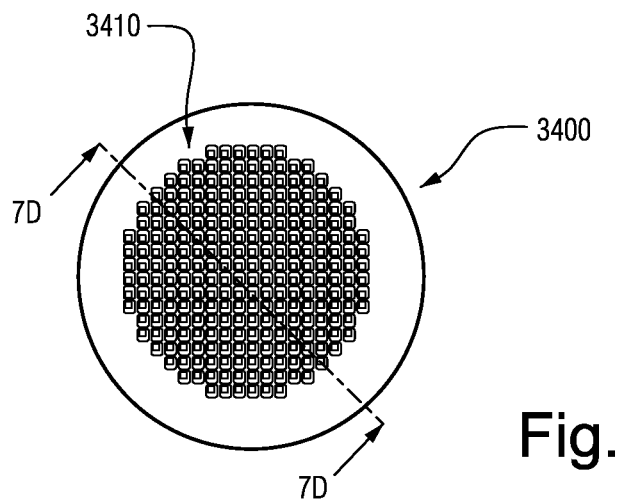

FIG. 7C shows the first side of a vent in accordance with an example of the present technology and indicates the position of a cross section 7D-7D.

Figure 7D:
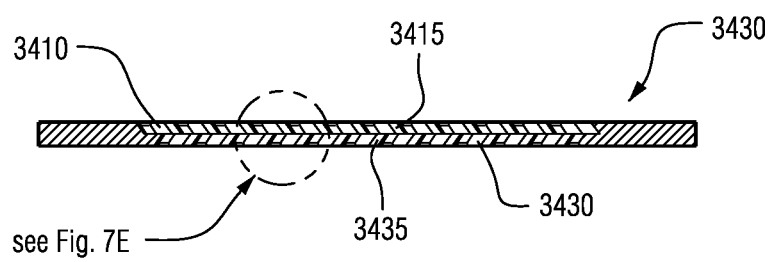

FIG. 7D shows a cross sectional view of the vent of FIG. 7C taken through line 7D-7D.

Figure 7E:
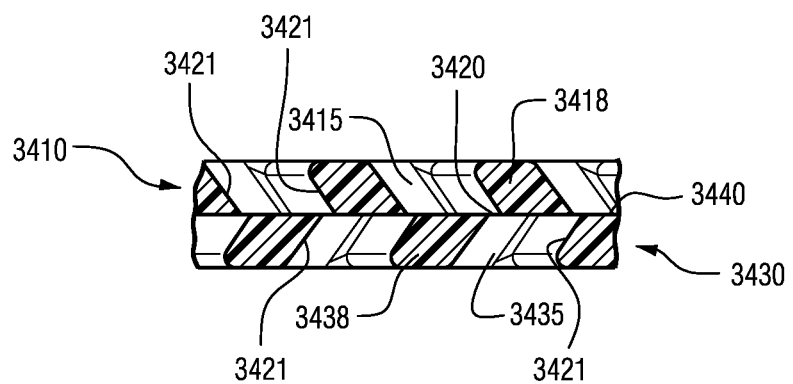

FIG. 7E shows a detailed view of the cross sectional view shown in FIG. 7D.

Figure 7F:
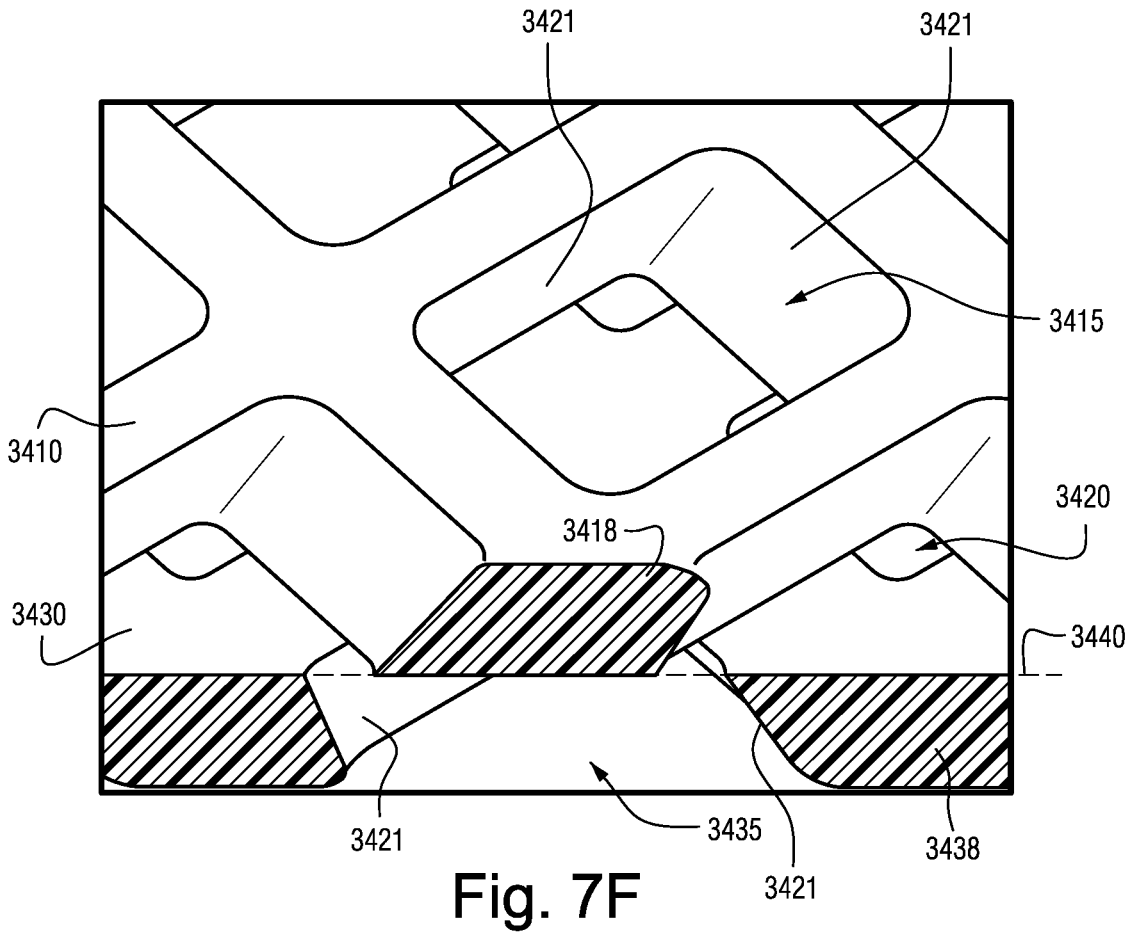

FIG. 7F shows another detailed cross-sectional view of the vent shown in FIG. 7C.

Figure 7G:
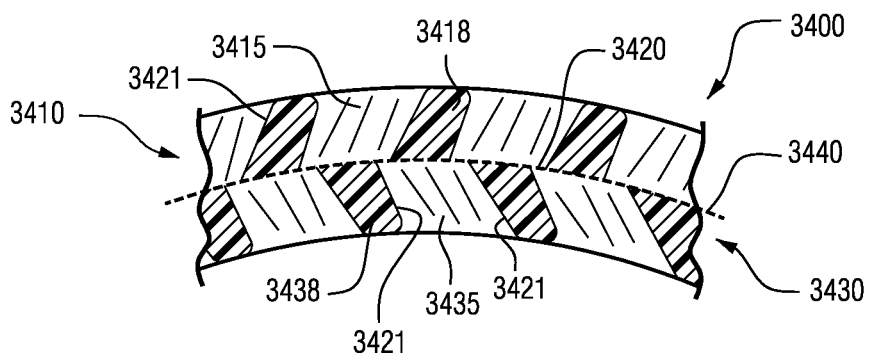

FIG. 7G shows a detailed cross sectional view of a curved vent in accordance with another form of the present technology.

FIG. 7H shows a detailed cross-sectional view of a vent shown in perspective according to another example of the present technology.

FIG. 7I shows a side view of the vent shown in FIG. 7A and indicates cross-section line 7J-7J.

FIG. 7J illustrates the top view of the cross section of the vent shown in FIG. 7I taken through line 7J-7J and shows a detailed view of the second side.

Figure 7K:
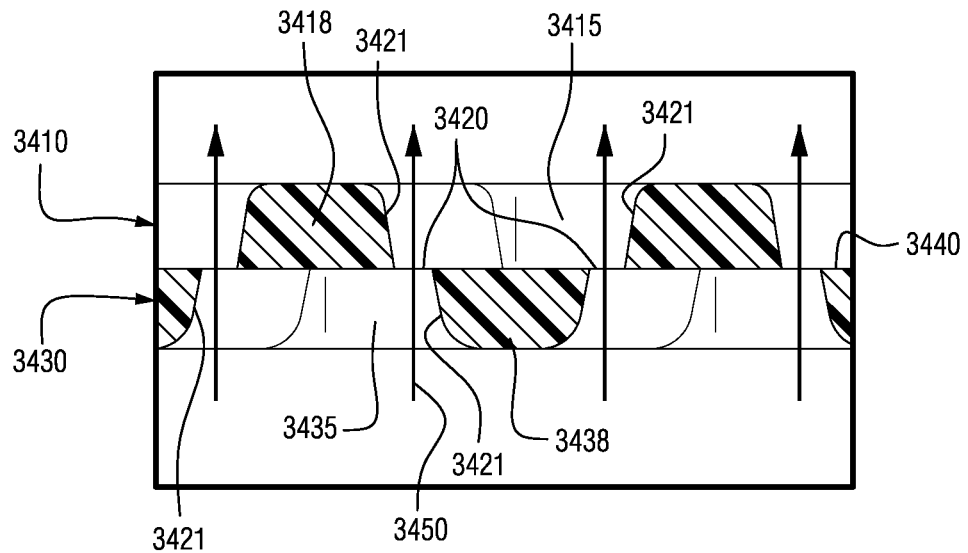

FIG. 7K illustrates a detailed cross sectional side view of the vent in accordance with another form of the present technology.

Figure 7L:
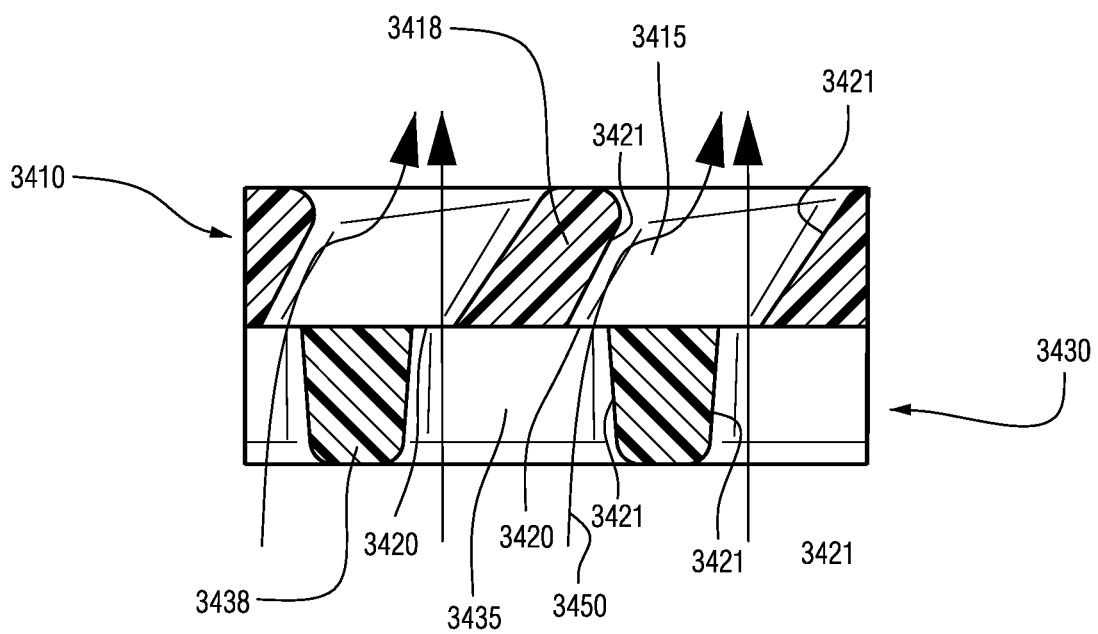

FIG. 7L illustrates a detailed cross sectional side view of the vent in accordance with another form of the present technology.

Figure 7M:
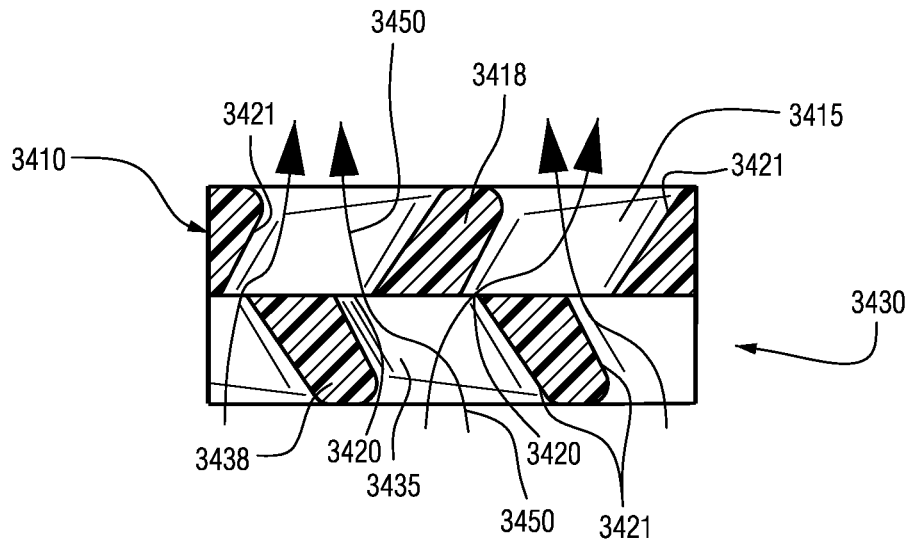

FIG. 7M illustrates a detailed cross sectional side view of the vent in accordance with another form of the present technology.

Figure 8A:
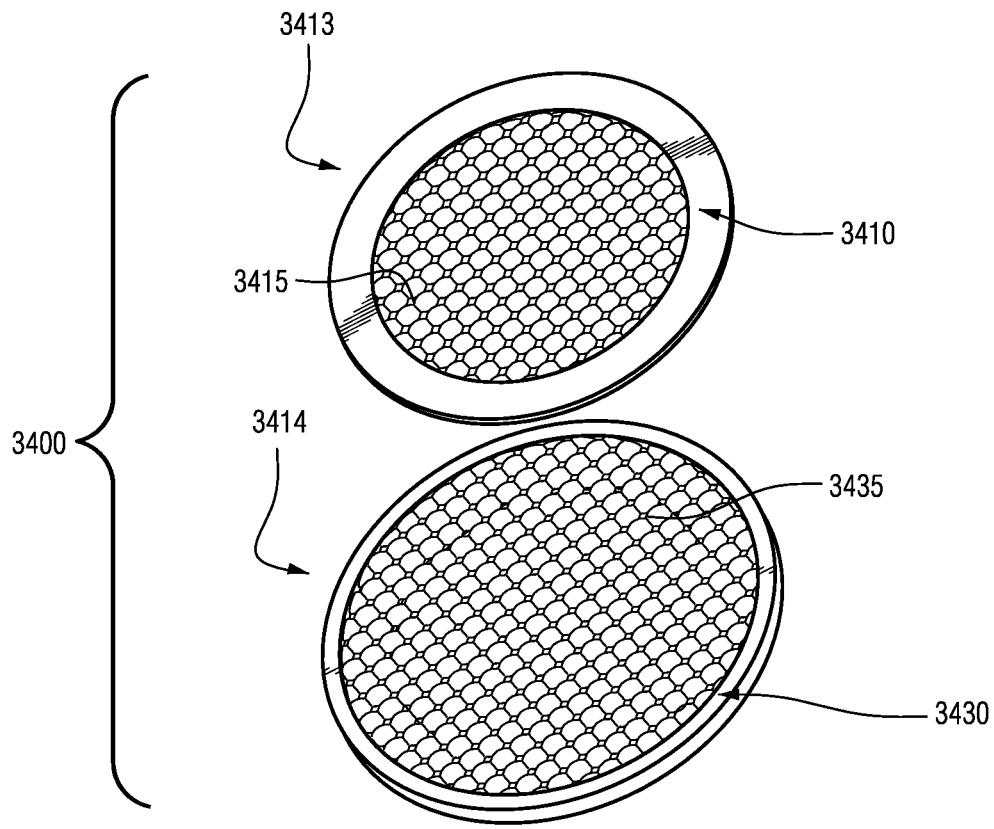

FIG. 8A shows perspective view of another form of the present technology having a first side and a second side in separate components.

FIG. 8B shows a cutaway perspective view of the vent of FIG. 8A.

FIG. 8C shows a detailed top view of the first side of the vent of FIG. 8A.

FIG. 8D shows a detailed perspective view of the first side of the vent of FIG. 8A.

Figure 8E:
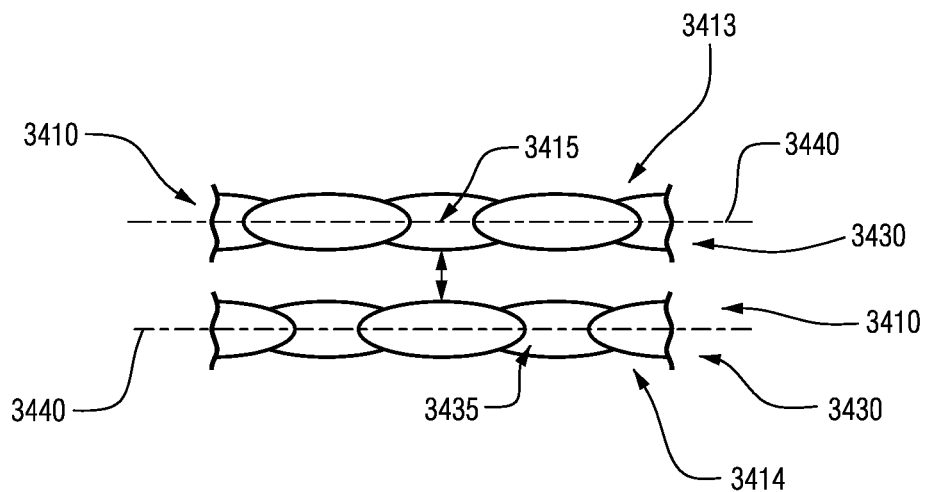

FIG. 8E shows a detailed cross sectional side view of the vent of FIG. 8A wherein the first side and second side are separated.

Figures 8F, 8G:
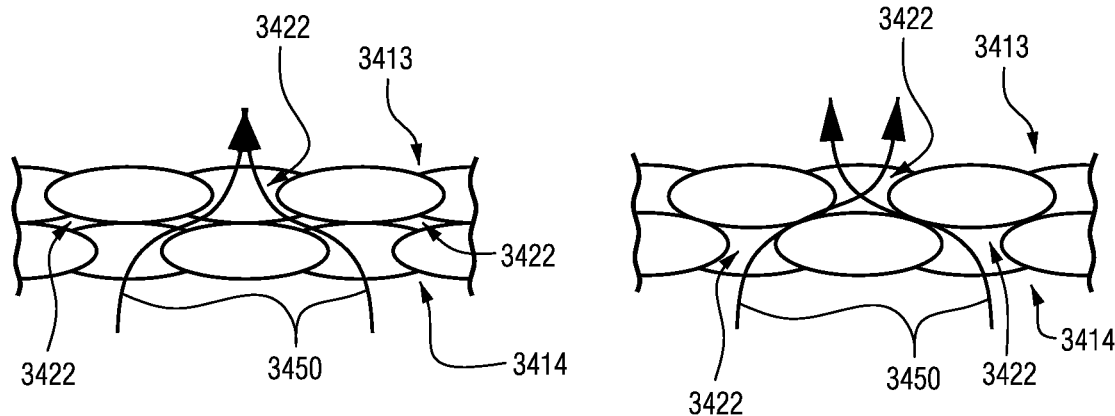

FIG. 8F illustrates a detailed cross sectional side view of the vent in accordance with another form of the present technology.

FIG. 8G illustrates a detailed cross sectional side view of the vent in accordance with another form of the present technology.

Figure 8H:
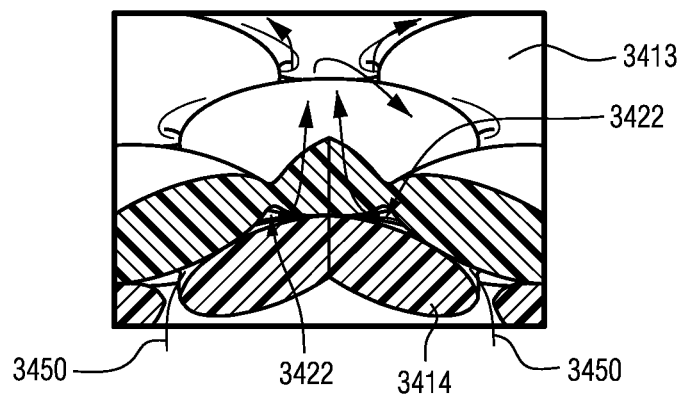

FIG. 8H illustrates a detailed cross sectional side view of the vent in accordance with another form of the present technology.

Figure 8I:
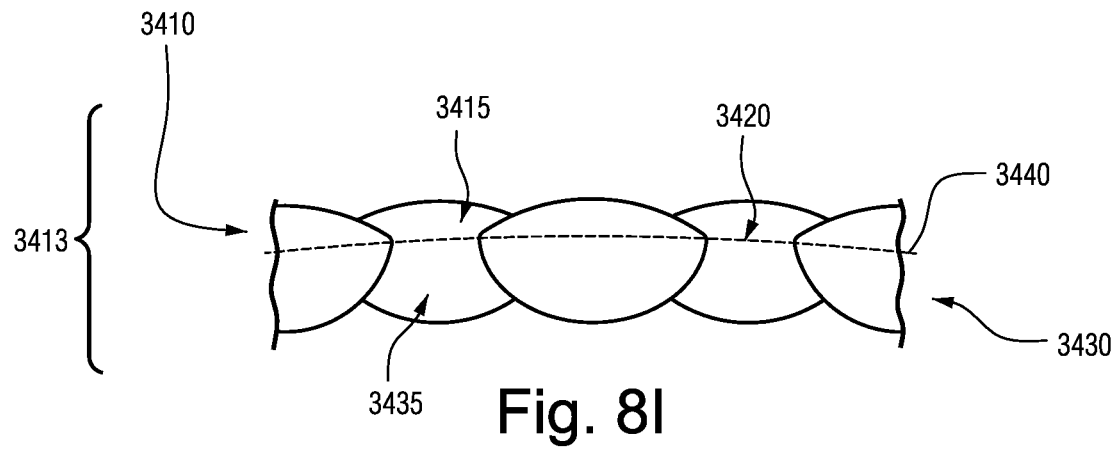

FIG. 8I illustrates a detailed cross sectional view of a curved vent in accordance with another form of the present technology.

Figure 8J:
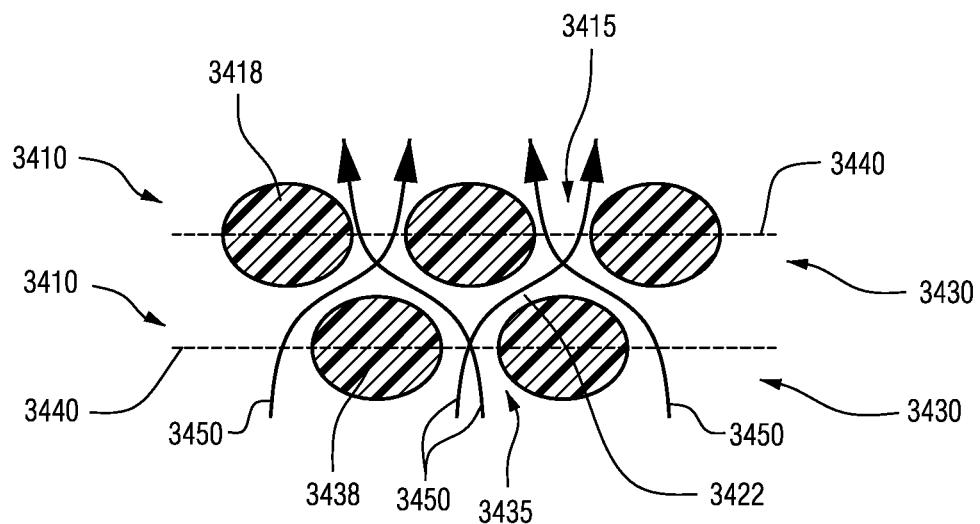

FIG. 8J illustrates a detailed cross sectional side view of the vent in accordance with another form of the present technology.

Figure 9A:
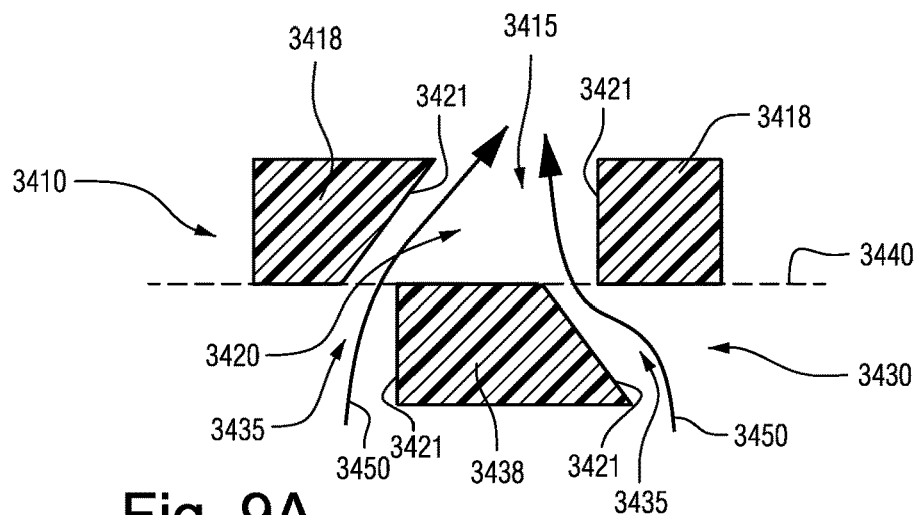

FIG. 9A illustrates a detailed cross sectional side view of the vent in accordance with another form of the present technology.

Figure 9B:
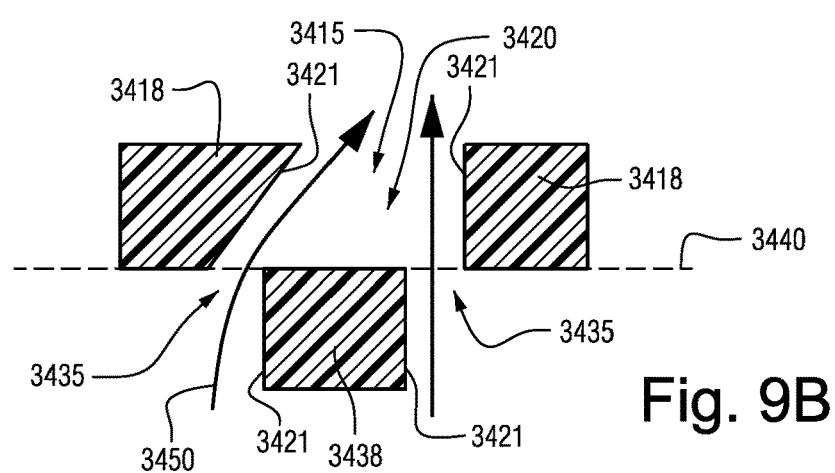

FIG. 9B illustrates a detailed cross sectional side view of the vent in accordance with another form of the present technology.

Figure 9C:
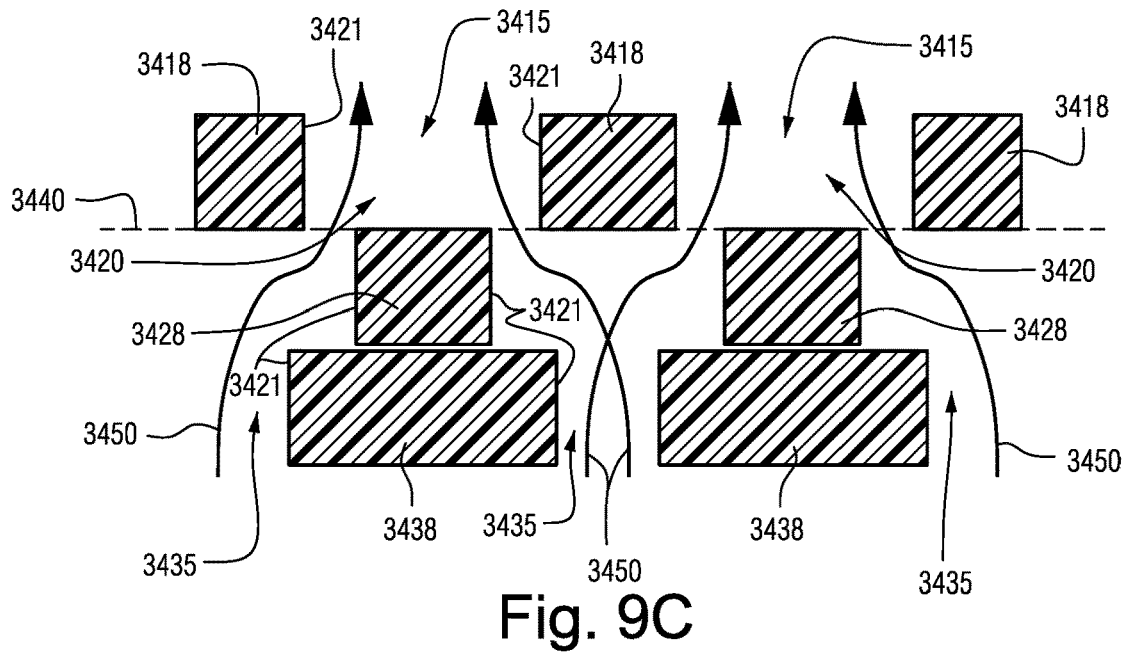

FIG. 9C illustrates a detailed cross sectional side view of the vent in accordance with another form of the present technology.

Figure 10:
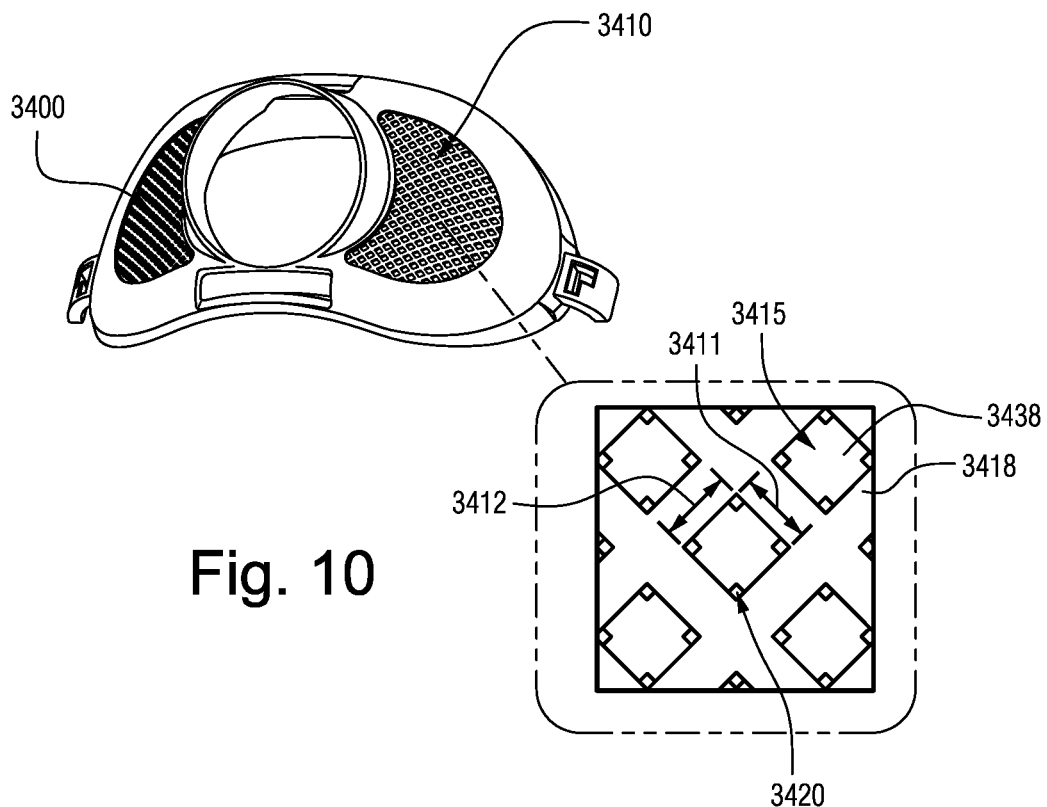

FIG. 10 shows a perspective view of a patient interface comprising a vent in accordance with the present technology, the figure illustrating a detailed view of the first side.

Figure 11A:
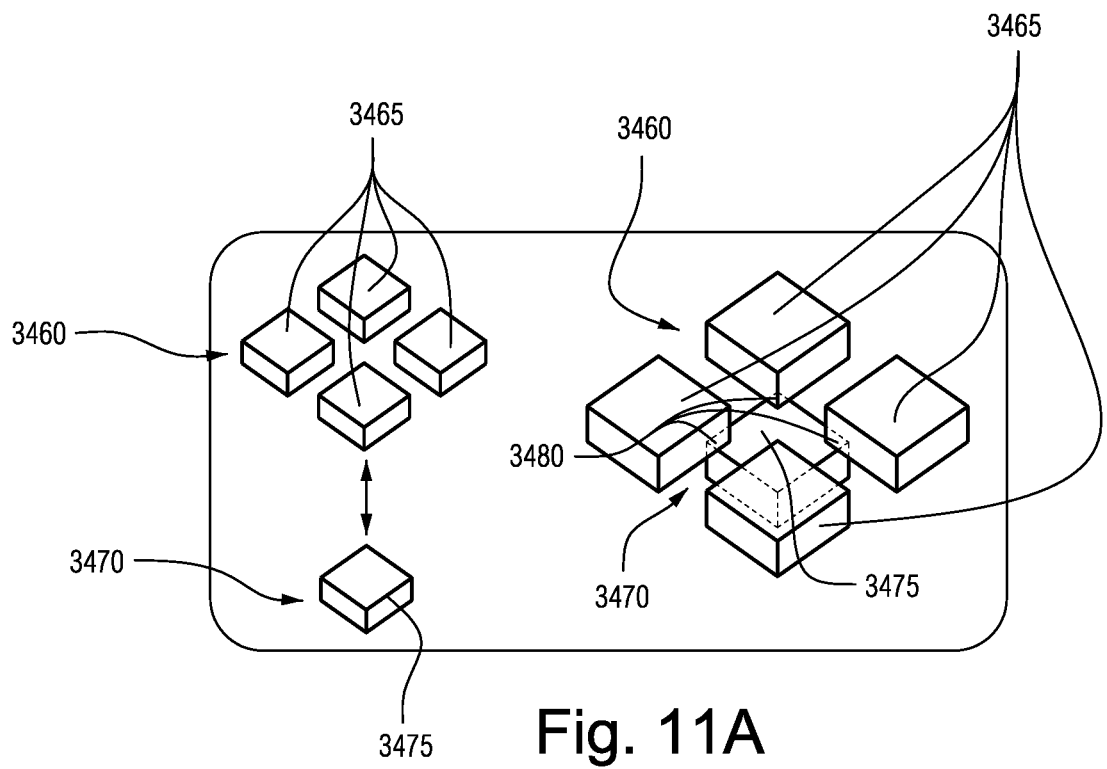

FIG. 11A illustrates a moulding tool for moulding a vent in accordance with the present technology.

Figure 11B:
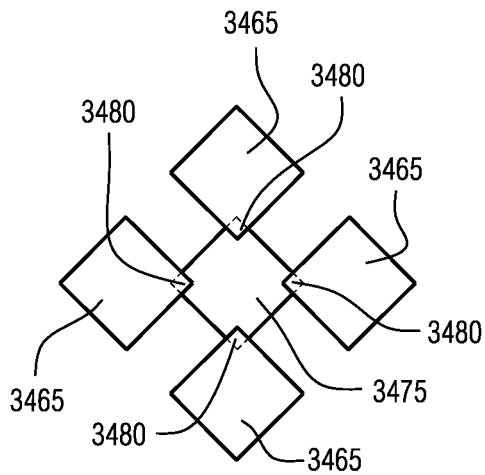

FIG. 11B shows a detailed schematic of partially overlapped pins of the moulding tool in accordance with the present technology.

Figure 11C:
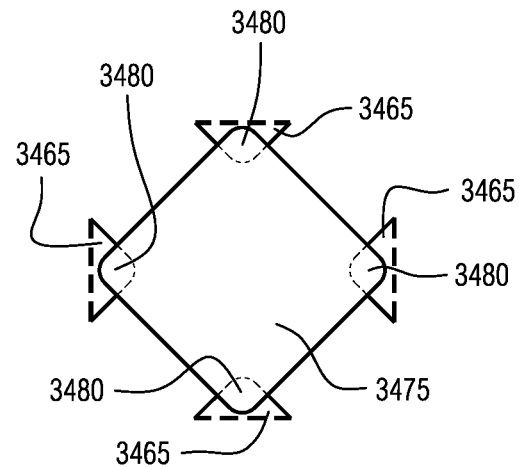

FIG. 11C shows a detailed schematic of partially overlapped pins of the moulding tool shown in FIG. 11A.

Figure 11D:
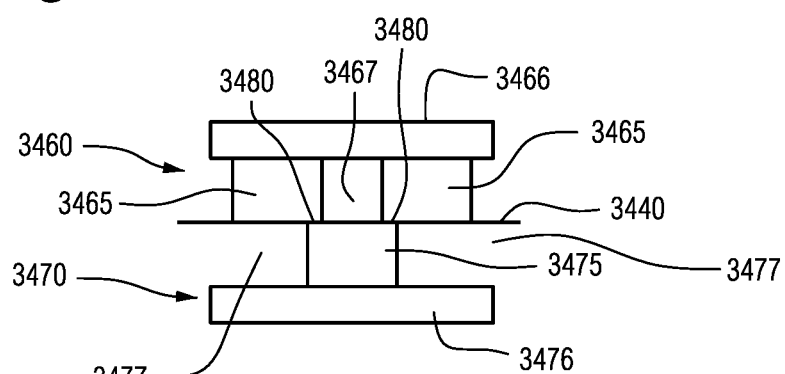

FIG. 11D shows a detailed side view of the pins of the moulding tool shown in FIG. 11A.

Figure 11E:
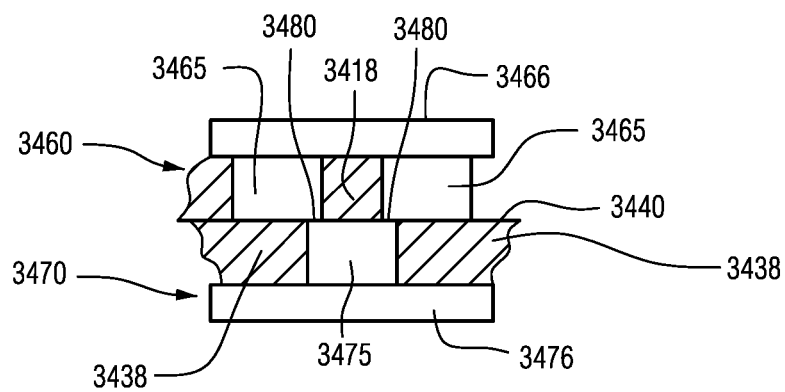

FIG. 11E shows a detailed side view of the pins of the moulding tool shown in FIG. 11A with moulding material added.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. The sealing flange comprises a relatively thin member with a thickness of less than about 1 mm, for example about 0.25 mm to about 0.45 mm, that extends around the perimeter of the plenum chamber 3200. Support flange 3120 may be relatively thicker than the sealing flange. The support flange 3120 is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

5.3.3 Positioning and Stabilising Structure

The seal-forming portion 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

5.3.4 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel 3510.

In another form in accordance with the present technology, the vent 3400 may comprise a first side 3410 and a second side 3430. The first side 3410 may comprise a plurality of first openings 3415. The first openings 3415 may be uniform in at least one of size and shape across the first side 3410. Each first opening 3415 extends from the first side 3410 towards the second side 3430 and terminate at a plane or an interface or an interface region 3440. The second side 3430 comprises a plurality of second openings 3435. The second openings 3435 may be uniform in at least one of size and shape across the second side 3430. Each second opening 3435 extends from the second side 3430 towards the first side 3410 and terminate at the plane 3440. The plurality of first openings 3415 may be positioned in an offset arrangement relative to the second openings 3435. For example, as shown in FIG. 7A, the first openings 3415 on the first side 3410 may be positioned such that they only partially overlap the second openings 3435 on the second side 3430. Each first opening 3415 may partially overlap at least one second opening 3435 along the plane 3440 to form a vent passage (e.g. a constricted passage 3420) therebetween, as shown in FIG. 7E. The plane 3440 may be a plane 3440 that runs in between the first 3410 and second sides 3430 and through the plurality of constricted passages 3420. The constricted passages 3420 may define the flow path 3450 for the flow of gas through the vent 3400. The plane 3440 may run horizontally between the first side 3410 and the second side 3430. The plane 3440 may also be curved, as shown in FIG. 7G. The first side 3410 may be substantially parallel to the second side 3430. Alternatively, the first side 3410 may and/or second side 3430 may comprise uneven surfaces that are non-parallel to each other.

The first openings 3415 may each be formed by a first wall 3418 that surrounds each first opening 3415. The first wall 3418 may be formed by a single curved surface that forms a single side 3421. Alternatively, the first wall 3418 may comprise a plurality of discrete sides 3421. For example, each first opening 3415 may comprise a plurality of sides 3421 to form a substantially cuboid shaped first opening 3415. Alternatively, the first openings may be formed by a single curved surface comprising a single side to form a substantially cylindrical shape such that the first opening 3415 is substantially circular in cross-section. Other shapes of the first openings 3415 may be formed to direct the desired flow characteristics of the flow of gas through the first openings 3415. For example, the first openings 3415 may be trapezoidal or triangular prism in shape or the first openings 3415 may have any other polygonal profile. Furthermore, the second openings 3435 may also be shaped in any of the ways described above for the first openings 3415. Additionally, the first openings 3415 and the second openings 3435 may be shaped differently from one another. The shape of each opening may be modified to provide the desired flow characteristics to achieve one or more of: a noise reduction, an increased diffuseness or a reduction in vent blockage under humidification.

The first walls 3418 forming the plurality of first openings 3415 may comprise an angled, tilted or curved side shape to direct the flow of gas through the opening in a predetermined orientation to decrease noise, increase diffuseness and/or decrease blockage under humidification. For example, the first walls 3418 may direct the flow of breathable gas along a surface of the first wall 3418 and through the first openings 3415, in a direction to diffuse the overall flow of gas exiting the vent 3400. Alternatively, the first walls 3418 may form a tortuous or crossover flow path to decrease noise and increase diffuseness. In one form of the present technology, the first opening depth 3419 may be 0.3 mm and the 3417 width and height 3416 of the first opening 3415 may be 0.5 mm. In another form, the first openings 3415 may be formed by a plurality of walls.

The second openings 3435 may each be formed by a second wall 3438 that surrounds each second opening 3435. The second wall 3438 may be formed by a single curved surface that forms a single side 3421. Alternatively, the second wall 3438 may comprise a plurality of discrete sides 3421. For example, each second opening 3435 may comprise a plurality of sides 3421 to form a substantially cuboid shaped second opening 3435. Alternatively, the second openings 3435 may be formed by a single curved surface comprising a single side 3421 to form a substantially cylindrical shape such that the second opening 3435 is substantially circular in cross-section. Other shapes of the second openings 3435 may be formed to direct the desired flow characteristics of the flow of gas through the second openings 3435. For example, the second openings 3435 may be trapezoidal or triangular prism in shape or the second openings 3435 may have any other polygonal profile. For example, the second walls 3438 may direct the flow of gas flowing through the second openings 3435, in a direction to diffuse the overall flow through the openings. Alternatively, the second walls 3438 may form a tortuous or crossover flow path to decrease noise and increase diffuseness. In another form of the present technology, the first openings 3415 may be angled relative to the second openings 3435 to direct the flow of gas through the vent in a predetermined orientation to diffuse the flow and reduce vent 3400 noise.

For example, the sides 3421 of each first wall 3418 in FIG. 7K are tilted toward one another such that each first opening 3415 increases in cross-sectional area away from the plane 3440. For example, the sides 3421 of each first wall 3418 may be tilted at an oblique (e.g., obtuse or acute) angle relative to the interface 3440. In other words, each first wall 3418 is thinner further from the interface 3440, while each first opening 3415 is wider. Similarly, the sides 3421 of each second wall 3438 are tilted toward one another such that each second opening 3435 increases in cross-sectional area away from the plane 3440. For example, the sides 3421 of each second wall 3438 may be tilted at an obtuse angle relative to the interface 3440. In other words, each second wall 3438 is thinner further from the interface 3440, while each second opening 3435 is wider. Thus, this arrangement provides a flow path 3450 through the constricted passages that is generally straight.

In one form of the present technology, the second opening depth 3439 may be 0.3 mm or about 0.3 mm and the width and the height of the second opening 3435 may each be 0.5 mm or about 0.5 mm. Each first opening 3415 may partially overlap a plurality of second openings 3435, while each second opening 3435 may simultaneously partially overlap a plurality of first openings 3415. For example, as depicted in FIG. 7H, each first opening 3415 may partially overlap four second openings 3435, while each second opening 3435 simultaneously partially overlaps four of the first openings 3415. In another form, the second openings 3435 may be formed by a plurality of walls 3438.

As illustrated in FIGS. 7E and 7H. Each first opening 3415 may at least partially overlap at least one second opening 3435 along the plane 3440 to form a constricted passage 3420 with a width and height of approximately 0.1 mm to approximately 0.15 mm. The first wall 3418 extends from the first side 3410 and terminate at the plane 3440 while the second wall 3438 extends from the second side 3430 and terminates at the plane 3440 on an opposing side to the first wall 3418. The first wall 3418 does not directly oppose the second wall 3438 thereby preventing water droplets from collecting therebetween to cause blockage under humidification. For example, the sloped sides in FIG. 7E allow any moisture that may condense on the vent 3400 to flow through the constricted passage.

In another form, the vent passage may be formed by a wall extending from the first side 3410 to the second side 3430. The wall forms the first opening 3415 extending from the first side 3410 and transitions towards the second side 3430 to form the second opening 3435, wherein the wall forms a stepped cross section to form the constricted passage 3420 between the first 3415 and second openings 3435.

In one form of the present technology shown in FIG. 7L, the first wall 3418 of each first opening 3415 may be angled relative to the second wall 3438 of the second opening 3435 such that the flow of breathable gas passing is directed to an angled flow path through the vent 3400. In the example shown in FIG. 7L, the sides 3421 of each first wall 3418 are tilted in substantially the same direction relative to the plane 3440. For example, one of the sides 3421 of the first wall 3418 is tilted relative to the interface 3440 at an obtuse angle and another one of the sides 3421 of the first wall 3418 is tilted relative to the interface 3440 at an acute angle. However, the sides 3421 of each second wall 3438 are tilted towards one another. For example, the sides 3421 of each second wall 3438 may be tilted relative to the interface 3440 at an obtuse angle. This arrangement results in differently shaped flow paths 3450 through the constricted passages 3420 such that one flow path 3450 follows a more tortuous or non-linear path, while an adjacent flow path 3450 is generally straight. Furthermore, such an arrangement may promote increased cross-flow of the flow paths 3450 to promote diffusion.

In another example of the present technology as illustrated in FIG. 7M, the first wall 3418 may be angled relative to the second wall 3438 such that the flow of gas flowing from the second opening 3435 and into the first opening 3415 may crossover the flow path of gas flowing from an adjacent second opening into the same first opening. In the example shown in FIG. 7M, the sides 3421 of each first wall 3418 are tilted in substantially the same direction relative to the plane 3440 and the sides 3421 of each second wall 3438 are also tilted in substantially the same direction relative to the plane 3440. For example, one of the sides 3421 of the first wall 3418 is tilted relative to the interface 3440 at an obtuse angle and another one of the sides 3421 of the first wall 3418 is tilted relative to the interface 3440 at an acute angle. For example, one of the sides 3421 of the second wall 3438 is tilted relative to the interface 3440 at an obtuse angle and another one of the sides 3421 of the second wall 3438 is tilted relative to the interface 3440 at an acute angle. However, the sides 3421 of each first wall 3418 and the sides 3421 of each second wall 3438 are tilted in opposite directions relative to one another. This arrangement may result in each flow path 3450 through each constricted passage 3420 being non-linear or tortuous. Furthermore, such an arrangement may promote increased cross-flow of the flow paths 3450 to promote diffusion.

Additional, exemplary arrangements of the vent 3400 according to the present technology are shown in FIG. 9A-9C.

In FIG. 9A, the first wall 3418 has one side 3421 that is tilted toward the second wall 3438 relative to the plane 3440 and another side 3421 that is substantially perpendicular to the plane 3440. The second wall 3418 also has one side 3421 that is tilted toward the first wall 3418 relative to the plane 3440 and another side 3421 that is substantially perpendicular to the plane 3440. The side 3421 of each respective wall 3418, 3438 that is tilted toward the other wall is located on opposite sides of the constricted passage 3420. As shown, this arrangement promotes cross-flow between the flow paths 3450.

In FIG. 9B, the first wall 3418 has one side 3421 that is tilted toward the second wall 3438 relative to the plane 3440 and another side 3421 that is substantially perpendicular to the plane 3440. The second wall 3418 has two sides 3421 that are both substantially perpendicular to the plane 3440. As shown, this arrangement promotes cross-flow between the flow paths 3450.

In FIG. 9C, the sides 3421 of the first wall 3418 and the second wall 3438 are substantially perpendicular to the plane 3440. There is also a third wall 3428 that has sides 3421 that are substantially perpendicular to the plane 3440. Also, the third wall 3428 is positioned between the first wall 3418 and the second wall 3438. Furthermore, the third wall 3428 is narrower than the first opening 3415 and the second wall 3438 to produce a staggered or stepped profile through the second opening 3435. As shown, this arrangement promotes cross-flow between the flow paths 3450.

In another form of the present technology, the vent may comprise a plurality of layers as shown in FIG. 8A. In some forms, the vent may include 3 or more layers, each spaced apart to form a plurality of constricted passages 3422 between adjacent layers. The vent may be formed by a first layer 3413 and a second layer 3414. Each layer may comprise a first side 3410 and a second side 3430. The first layer 3413 may be removably or permanently attached to the second layer 3414. The first side 3410 may comprise a plurality of first openings 3415, the first openings may have a width 3417 of approximately 0.5 mm. Similarly, the second side 3430 may comprise a plurality of second openings 3435, which may also have a width 3417 of approximately 0.5 mm. The first openings 3415 may partially overlap the second openings 3435 at the plane 3440 to form the constricted passage 3420. As shown in FIG. 8I, the plane 3440 may be curved to correspond to the curvature of the patient interface 3000, such as the curvature of the plenum chamber 3200, in which the vent 3400 is positioned. The plane 3440 may be curved in a plurality of directions, such as along two orthogonal directions, for example according to curvatures of a plenum chamber 3200. The walls of one or both of the first layer 3413 and the second layer 3414 forming the first openings 3415 and second openings 3435 may be curved as depicted in FIGS. 8E to 8J, or comprise curved portions. As illustrated, the first openings 3415 have a reducing cross-sectional area such that they converge towards the constricted passage 3422. Similarly, the second openings 3435 also converge towards the constricted passage 3422. As shown in FIGS. 8F and 8J, the first layer 3413 may also be spaced apart from the second layer 3414 to provide an additional constricted passage 3422 between the layers. The additional constriction enhances noise reduction and increases diffuseness of the vent 3400.

As depicted in FIG. 10, the vent 3400 may be positioned on the plenum chamber 3200 of the patient interface 3000. The first side 3410 of the vent may face the external environment of the patient interface 3000, while the second side 3430 may face the internal chamber or plenum chamber 3200 of the patient interface 3000. The vent 3400 may be positioned such that when in use the exhaled gases of the patient flow into the second openings 3435 on the second side 3430 of the vent, through the constricted passages 3420 and pass through the first openings 3415 to exit the vent. The constricted passages provide a means of increasing the diffuseness of the flow and reducing vent noise without being vulnerable to vent blockage by water drops collecting in the vent holes under humidification. Moreover, the wall or walls forming the first openings 3415 and second openings 3435 may also be structured to enhance desired flow characteristics of the exhaled gas flow to increase diffuseness and decrease noise by directing the flow into a desired orientation.

In another form of the present technology, the vent 3400 may be positioned on a connector such as an elbow or swivel connector that connects the patient interface 3000 to an air delivery tube or conduit. Alternatively, the vent 3400 may be positioned on the air delivery tube or conduit.

5.3.5 Vent Manufacturing

In one form in accordance with the present technology, the vent 3400 may be manufactured by moulding the vent 3400 using a moulding tool comprising a tool first side 3460 and a tool second side 3470. The tool first side 3460 may comprise a plurality of first pins 3465 and the tool second side 3470 may comprise a plurality of second pins 3475. The plurality of first pins 3465 and the plurality of second pins may be moveable towards each other until they engage along the plane 3440. The first pins 3465 may only partially overlap the second pins 3475 along the plane 3440. Moulding material may be added to the tool and set around the pins such that the first openings 3415 and second openings 3435 are formed around their respective first pins 3465 and second pins 3475. The constricted passages 3420 may be formed around the locations of pin partial overlap 3480 such that the plane 3440 runs through the constricted passages 3420. The first pins 3465 and the second pins 3475 may retract away from each other to demould the vent 3400 once the moulding material is set within the tool. Alternatively, either of the first pins 3465 or the second pins 3475 may retract such that the vent 3400 may be demoulded from the remaining pins. The thickness and length of the first pins 3465 and second pins 3475 may be modified to form the respective first openings 3415 and second openings 3435 of a predetermined shape and size. The pins may have a thickness of approximately 0.3 to approximately 1 mm, or approximately 0.5 mm to prevent breakage or deformation under use. The total surface area of the pin partial overlap 3480 may be adjusted to form a constricted passage 3420 having a predetermined cross sectional area. The total surface area of the pin partial overlap 3480 may be approximately 0.05 to approximately 0.2 mm$^2$, or approximately 0.1 mm$^2$.

FIGS. 11D and 11E depict the moulding process. FIG. 11D shows the first side 3460 of the tool having the first pins 3465 joined to a first base 3466 and the first pins 3465 define a first void 3467. The second side 3470 of the tool also has the second pins 3475 joined to a second base 3476 and the second pins 3475 define second voids 3477. FIG. 12E shows the first void 3467 and the second void 3477 filled in with the material of the vent 3400 to form the first wall 3418 and the second wall 3438, respectively. When the tool is removed from the vent 3400, may be the vent 3400 depicted in FIG. 7A, for example.

It should be understood that the manufacturing process depicted in FIGS. 11A-11E could be extrapolated to produce a vent 3400 of sufficient size for use in a patient interface 3000. In other words, the tool to produce the vent 3400 would include many first pins 3465 and second pins 3475 to produce a vent 3400 with many first openings 3415 and second openings 3435. Furthermore, the number and size of the openings produced by the pins may be selected to yield predetermined flow characteristics. This method of manufacturing also allows for each vent 3400 to be produced substantially identically as compared to a woven vent, for example, that may have blockages and other variabilities due to the fibers of the weave pattern. Additionally, this method of manufacturing the vent 3400 allows for precise control of the size, number, and shape of the openings and, therefore, the flow characteristics of the vent. These improvements over a mesh or woven vent are also possible while maintaining substantially the same diffuseness as a mesh or woven vent and substantially the same level of noise reduction.

An alternative method of manufacturing the vent 3400 may include molding each wall 3418, 3438 separately and then securing the separate walls together. The examples show in FIGS. 8A and 8B may also be manufactured in such a manner.

Alternatively, the vent 3400 may be formed by drilling, milling or laser cutting the first openings 3415 and/or second openings 3435 to the predetermined cross sectional area, such that the first openings 3415 only partially overlap the second openings 3435 to from a constricted passage 3420 therebetween. In this alternative manufacturing method, the vent 3400 may begin as a solid piece of material and then drilling, milling or laser cutting produces the first openings 3415 and/or second openings 3435. Additionally, or alternatively, the vent 3400 may be formed by an additive method, such as three-dimensional printing.

5.3.6 Decoupling Structure(s)

In one form the patient interface 3000 includes at least one decoupling structure 3500, for example, a swivel 3510 or a ball and socket 3520.

5.3.7 Connection Port

Connection port 3600 allows for connection to the air circuit 4170.

5.3.8 Forehead Support

In one form, the patient interface 3000 includes a forehead support 3700.

5.3.9 Anti-Asphyxia Valve

In one form, the patient interface 3000 includes an anti-asphyxia valve 3800.

5.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

5.5 Humidifier

5.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is continuously positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is continuously adjustable, e.g. from breath to breath, between minimum and maximum limits, depending on the presence or absence of indications of SDB events.

5.7.2 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate may be given the symbol Q. 'Flow rate' is sometimes shortened to simply 'flow'.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.7.3 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240 (year?required??)

Polycarbonate: a typically transparent thermoplastic polymer of Bisphenol-A Carbonate.

5.7.4 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows a flow of air from an interior of the mask, or conduit, to ambient air to allow clinically effective washout of exhaled gases. For example, a clinically effective washout may involve a flow rate of about 10 litres per minute to about 100 litres per minute, depending on the mask design and treatment pressure.

5.7.5 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.
Unable to retain its shape when caused to support its own weight.
Not rigid.
Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

5.8 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| Part References | Numbers |
|---|---|
| patient | 1000 |
| bed partner | 1100 |
| patient interface | 3000 |
| seal-forming structure | 3100 |
| plenum chamber | 3200 |
| position and stabilising structure | 3300 |
| vent | 3400 |
| first side | 3410 |
| first layer | 3413 |
| second layer | 3414 |
| first opening | 3415 |
| first opening height | 3416 |
| first opening height width | 3417 |
| first wall | 3418 |
| first opening depth | 3419 |
| constricted passage | 3420 |
| side | 3421 |
| constricted passage | 3422 |
| second side | 3430 |
| second opening | 3435 |
| second wall | 3438 |
| second opening depth | 3439 |
| plane | 3440 |
| tool first side | 3460 |
| first pins | 3465 |
| first base | 3466 |
| first void | 3467 |
| tool second side | 3470 |
| second pins | 3475 |
| second base | 3476 |
| second void | 3477 |
| pin partial overlap | 3480 |
| decoupling structure | 3500 |
| one decoupling structure | 3500 |
| swivel | 3510 |
| socket | 3520 |
| connection port | 3600 |
| forehead support | 3700 |
| anti-asphyxia valve | 3800 |
| rpt device | 4000 |
| external housing | 4010 |
| upper portion | 4012 |
| lower portion | 4014 |
| panels | 4015 |
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| inlet muffler | 4122 |
| outlet muffler | 4124 |
| pressure generator | 4140 |
| blower | 4142 |
| motor | 4144 |
| air circuit | 4170 |
| electrical components | 4200 |
| PCBA | 4202 |
| power supply | 4210 |
| input device | 4220 |
| central controller | 4230 |
| therapy device controller | 4240 |
| protection circuits | 4250 |
| memory | 4260 |
| transducer | 4270 |
| pressure sensor | 4272 |
| flow rate sensors | 4274 |
| data communication interface | 4280 |
| output device | 4290 |
| algorithms | 4300 |
| humidifier | 5000 |
| humidifier inlet | 5002 |
| humidifier outlet | 5004 |
| humidifier base | 5006 |
| reservoir | 5110 |
| conductive portion | 5120 |
| reservoir dock | 5130 |
| locking lever | 5135 |
| water level indicator | 5150 |
| heating element | 5240 |

The invention claimed is:

1. A patient interface for sealed delivery of a flow of air at a continuously positive pressure with respect to ambient air pressure to an entrance to a patient's airways including at least the patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing, the patient interface comprising:
a sealing structure comprising a flange configured to seal against an area of the patient's face surrounding an entrance to the patient's airways;
a plenum chamber connected to the sealing structure and configured to be pressurised to the therapy pressure in use;
a positioning and stabilising structure comprising a strap configured to maintain the sealing structure in sealing contact with the patient's face in use; and
a gas washout vent configured to allow a vent flow of gas to exit the plenum chamber to atmosphere to minimise rebreathing of exhaled gas by the patient, the gas washout vent comprising:
a first layer having a plurality of first openings arranged in first rows and first columns to form a first grid; and
a second layer having a plurality of second openings arranged in second rows and second columns to form a second grid,
wherein the first layer and the second layer are attached to one another such that the first openings and the second openings are offset relative to each other to form a plurality of constricted passages extending through the first openings and the second openings of the first layer and the second layer, respectively, to allow the vent flow of gas to pass through the gas washout vent to atmosphere, and
wherein a first axis is defined through each of the first openings, the first axes being parallel to one another, and a second axis is defined through each of the second openings, the second axes being parallel to one another, and
wherein the first axes are oriented at a different angle than the second axes.

2. The patient interface of claim 1, wherein the first layer and the second layer are permanently attached to one another.

3. The patient interface of claim 1, wherein the first layer and the second layer are curved.

4. The patient interface of claim 1, wherein the first layer and the second layer are flat.

5. The patient interface of claim 1, wherein each of the first openings partially overlaps more than one of the second openings.

6. The patient interface of claim 5, wherein each of the first openings has a substantially constant cross sectional area through the first layer that is larger than a cross sectional area of a corresponding one of the constricted passages.

7. The patient interface of claim 6, wherein each of the second openings has a substantially constant cross sectional area through the second layer that is larger than a cross sectional area of a corresponding one of the constricted passages.

8. The patient interface of claim 1, wherein each of the second openings partially overlaps more than one of the first openings.

9. The patient interface of claim 1, wherein each of the first openings and each of the second openings is a cube or a cuboid in shape.

10. The patient interface of claim 1, wherein each of the second openings is a cube or a cuboid in shape.

11. The patient interface of claim 1, wherein the first openings are uniform in size and shape, and wherein the second openings are uniform in size and shape.

12. The patient interface of claim 11, wherein the first openings are different in at least one of shape and size from the second openings.

13. The patient interface of claim 11, wherein the first openings and the second openings are the same in at least one of shape and size.

14. The patient interface of claim 1, wherein the gas washout vent is located on the plenum chamber.

15. The patient interface of claim 1, further comprising an elbow configured to connect the patient interface to an air circuit, the gas washout vent being located on the elbow.

16. The patient interface of claim 1, wherein each of the first openings and each of the second openings are formed by at least one curved wall.

17. The patient interface of claim 1, wherein each of the first openings and each of the second openings are formed by at least one wall that is slanted at different angle relative to at least one other wall.

18. The patient interface of claim 1, wherein each of the first openings and each of the second openings are formed by at least one flat wall.

* * * * *